US012799088B2

(12) United States Patent
Collina et al.

(10) Patent No.: US 12,799,088 B2
(45) Date of Patent: Nov. 17, 2026

(54) SUBSTITUTED VINYL PIPERAZINE-PIPERIDINE UREA DERIVATIVES AS ANTICANCER AGENTS

(71) Applicants: UNIVERSITA' DEGLI STUDI DI PAVIA, Pavia (IT); UNIVERSITÀ DEGLI STUDI DI MILANO-BICOCCA, Milan (IT)

(72) Inventors: Simona Collina, Pavia (IT); Daniela Rossi, Vigevano (IT); Pasquale Linciano, Nardo (IT); Giacomo Rossino, Robbio (IT); Roberta Listro, Palermo (IT); Marco Peviani, Santo Stefano Lodigiano (IT); Silvia Stefania Rossi, San Martino Siccomario (IT); Barbara Vigani, Pavia (IT); Guido Angelo Cavaletti, Guido (IT); Mariarosaria Miloso, Monza (IT); Alessio Malacrida, Milan (IT)

(73) Assignees: UNIVERSITA' DEGLI STUDI DI PAVIA, Pavia (IT); UNIVERSITA' DEGLI STUDI DI MILANO-BICOCCA, Milan (IT)

( * ) Notice: Subject to any disclaimer, the term of this patent is extended or adjusted under 35 U.S.C. 154(b) by 338 days.

(21) Appl. No.: 18/698,459

(22) PCT Filed: Jun. 20, 2022

(86) PCT No.: PCT/EP2022/066667
§ 371 (c)(1),
(2) Date: Apr. 4, 2024

(87) PCT Pub. No.: WO2023/057097
PCT Pub. Date: Apr. 13, 2023

(65) Prior Publication Data

US 2025/0236600 A1 Jul. 24, 2025

(30) Foreign Application Priority Data

Oct. 7, 2021 (EP) .................................... 21201359

(51) Int. Cl.

| | |
|---|---|
| ***C07D 295/215*** | (2006.01) |
| ***A61K 31/445*** | (2006.01) |
| ***A61K 31/495*** | (2006.01) |
| ***A61P 35/00*** | (2006.01) |
| ***C07D 211/16*** | (2006.01) |
| ***C07D 211/22*** | (2006.01) |
| ***C07D 211/34*** | (2006.01) |

(52) U.S. Cl.
CPC ........ *C07D 295/215* (2013.01); *A61K 31/445* (2013.01); *A61K 31/495* (2013.01); *A61P 35/00* (2018.01); *C07D 211/16* (2013.01); *C07D 211/22* (2013.01); *C07D 211/34* (2013.01)

(58) Field of Classification Search
CPC .............. C07D 295/215; C07D 211/16; C07D 211/22; C07D 211/34
See application file for complete search history.

(56) References Cited

U.S. PATENT DOCUMENTS

| | | | |
|---|---|---|---|
| 8,173,653 | B2 | 5/2012 | Dorsch et al. |
| 8,367,668 | B2 | 2/2013 | Stieber et al. |
| 8,765,740 | B2 | 7/2014 | Li et al. |
| 9,278,940 | B2 | 3/2016 | Fairfax et al. |
| 9,447,049 | B2 | 9/2016 | Dalton et al. |
| 10,913,750 | B2 | 2/2021 | Torres et al. |
| 11,241,500 | B2 | 2/2022 | Moreau et al. |
| 11,945,805 | B2 | 4/2024 | Chen et al. |
| 2007/0027184 | A1 | 2/2007 | Malecha et al. |
| 2011/0301157 | A1 | 12/2011 | Bold et al. |
| 2019/0185509 | A1 | 6/2019 | Birkus et al. |
| 2022/0096640 | A1 | 3/2022 | Moreau et al. |
| 2023/0101559 | A1 | 3/2023 | Bogdan et al. |
| 2024/0052049 | A1 | 2/2024 | Barnes et al. |

FOREIGN PATENT DOCUMENTS

| | | | | |
|---|---|---|---|---|
| CA | 3078267 A1 | 5/2019 | | |
| CA | 3084582 A1 | 6/2019 | | |
| CN | 110392580 A | 10/2019 | | |
| CN | 113195487 A | 7/2021 | | |
| JP | 61-291579 | * 12/1986 | ........... C07D 295/18 | |
| TW | 202100163 A | 1/2021 | | |

OTHER PUBLICATIONS

Cheng Wang, et al. "Celastrol as an emerging anticancer agent: Curren status, challenge and therapeutic strategies", Biomedicine Pharmacotherapy, "State Key Laboratory of Southwestern Chinese Medicine Resources, Minstry of education, school of pharmacy, chengdu University of traditional chinese Medicine, Chengdu 611137, China" vol. 163, Jul. 2023, 114882, https://doi.org/10.1016/j.biopha.2023.114882 ; https://www.sciencedirect.com/science/article/pii/S0753332223006728.

Chiara Brullo, Federica Rapetti, Olga Bruno, "Pyrazolyl-Ureas as Interesting Scaffold in Medicinal chemistry", Department of Pharmacy, Section of Medicinal Chemistry, University of Genoa, Viale Benedetto XV 3, I-16132 Genova, Italy, Jul. 29, 2020, https://doi.org/10.3390/molecules25153457 https://www.mdpi.com/1420-3049/25/15/3457.

(Continued)

*Primary Examiner* — Laura L Stockton
(74) *Attorney, Agent, or Firm* — Carmel Patent Agency; Robert Ballarini

(57) ABSTRACT

The present invention is comprised in the field of medicinal chemistry, and it is related to substituted vinyl piperazine-piperidine urea compound which are well effective as anti-tumoral agents. In particular, they are suitable in methods of treatment of glioblastoma (GB), multiple myeloma (MM) or pancreatic cancer (PC).

17 Claims, 11 Drawing Sheets

(56) References Cited

OTHER PUBLICATIONS

Rongshi Li, Alan Pourpak, Stephan W. Morris, "Inhibition of the Insulin-like Growth Factor-1 Receptor (IGF1R) Tyrosine Kinase as a Novel Cancer Therapy Approach", J Med Chem.Aug. 27, 2009; 52(16): 4981-5004, 10.1021/jm9002395 https://www.ncbi.nlm.nih.gov/pmc/articles/PMC2888655/.

Cappellacci, Loredana, Perinelli, diego R., Maggi, Filippo, Grifantini, Mario, Petrelli, Riccardo, "Recent Progress in Histone Deacetylase Inhibitors as Anticancer Agents", Current Medicinal Chemistry, vol. 27, No. 15, 2020, pp. 2449-2493(45), https://doi.org/10.2174/0929867325666181016163110 https://www.ingentaconnect.com/content/ben/cmc/2020/00000027/00000015/art00003 , Abstract Only Provided.

Giovanni Marzaro, Adriano Guiotto, Adriana Chilin, "Quinazoline derivatives as potential anticancer agents: a patent review (2007-2010)", Padova Italy, vol. 22, 2012—Issue 3, Mar. 12, 2012, https://www.researchgate.net/publication/221690169 https://www.tandfonline.com/doi/abs/10.1517/13543776.2012.665876.

Laura Gallego-Yerga, Valentin Cena, Rafael Pelaez, "Potent and Selective Benzothiazole-Based Antimitotics with Imroved Water Solubility: Design, Synthesis, and Evaluation as Novel Anticancer Agents", Campus Miguel de Unamuno, 37007 Salamanca, Spain, Jun. 9, 2023, https://doi.org/10.3390/pharmaceutics15061698 https://www.mdpi.com/1999-4923/15/6/1698.

H. Hatcher, R. Planalp, J. Cho, F.M. Torti, S.V.Torti, "Curcumin: From ancient medicine to current clinical trials", Cellular and Molecular Life Science, Mar. 7, 2008, Voulme 65, pp. 1631-1652, (2008), doi: 10.1007/s00018-008-7452-4 https://www.ncbi.nlm.nih.gov/pmc/articles/PMC4686230/?fbclid=IwAR0vU13_Po4voz-crMmNYU7-1a1P94n-3udNa1bKPyZd7edp6PoLQdn8nlk.

Ahmed M. Shawky, et al. "Pharmacophore-based virtual screening, synthesis, biological evaluation, and molecular docking study of novel pyrrolizines bearing urea/thiourea moieties with potentia cytotoxicity and CDK inhibitory activities", Journal of Enzyme Inhibition and Medicinal Chemistry, vol. 36, 2021—Issue 1, Oct. 26, 2020, pp. 15-33, https://doi.org/10.1080/14756366.2020.1837124 ; https://www.tandfonline.com/doi/full/10.1080/14756366.2020.1837124.

* cited by examiner $^1H$ NMR (300 MHz, $CDCl_3$) N-cyclopentyl-4-[(2E)-3-(naphthalen-2-yl)but-2-en-1-yl]piperazine-1-carboxamide

$^{13}$C NMR (100 MHz, $CDCl_3$) *N*-cyclopentyl-4-[(2*E*)-3-(naphthalen-2-yl)but-2-en-1-yl]piperazine-1-carboxamide $^{1}H$ NMR (300 MHz, $CDCl_3$) *N*-cyclohexyl-4-[(2*E*)-3-(naphthalen-2-yl)but-2-en-1-yl]piperazine-1-carboxamide $^{13}C$ NMR (100 MHz, $CDCl_3$) *N*-cyclohexyl-4-[(2*E*)-3-(naphthalen-2-yl)but-2-en-1-yl]piperazine-1-carboxamide

$^1$H NMR (300 MHz, $CDCl_3$) *N*-(2,6-difluorophenyl)-4-[(2*E*)-3-(6-methoxynaphthalen-2-yl)but-2-en-1-yl]piperazine-1-carboxamide $^{13}C$ NMR (100 MHz, $CDCl_3$) *N*-(2,6-difluorophenyl)-4-[(2*E*)-3-(6-methoxynaphthalen-2-yl)but-2-en-1-yl]piperazine-1-carboxamide Cell viability of U87-MG cells Cell viability of RPMI 8226 cells Cell migration of U87-MG cells Cell invasion of U87-MG and RPMI 8226 cells Proteasome activity of U87-MG and RPMI 8226 cells Neurite outgrowth of embryonic rat DRG organotypic cultures

SUBSTITUTED VINYL PIPERAZINE-PIPERIDINE UREA DERIVATIVES AS ANTICANCER AGENTS

FIELD OF INVENTION

The present invention is comprised in the field of medicinal chemistry, and it is related to a novel series of urea derivatives as antitumoral agents.

STATE OF THE ART

Cancer disease represents one of the main causes of death worldwide Despite the relevant progress achieved by academia and pharma-company on diagnosis and treatments of cancer, today several tumors are considered uncurable and represent an urgent medical need. Among the different type of cancers, glioblastoma (GB), multiple myeloma (MM) and pancreatic cancer (PC) are mainly investigated for their impact on the society in terms of patients quality of life, difficulty to diagnose, increasing incidence and mortality.

GB is a most common malignant recurrent astrocytic tumor (IV grade according to the WHO classification) in adults with an annual incidence of 3.1 per 100000 people and 70% of cases are diagnosed at ages between 45 and 70 years. It is often aggressive and grows into surrounding normal brain tissues. The cause of the tumor is not known, except in case of therapeutic brain irradiation performed as therapy for other diseases.

Starting from the origin of tumor, two type of GB have been recognized: primary GB (de novo) or secondary GB (that develops from a benign astrocytic tumor). The symptoms are not specific (such as headache and nausea) and neurological signs are secondary to intracranial hypertension, in association with changes in behavior or focal neurological deficit. Surgery, chemotherapy and radiotherapy allow to get more lifetime to patients.

The execution of surgical treatment, including both biopsy and the partial or complete resection, depends on the tumor location and the age of the patients. After the initial tumor resection, radiotherapy and chemotherapy have been employed in GB treatment and specifically temozolomide, an oral alkylating agent, is the first-choice drug used. The most limiting issue of this pathology are the tumor aggressiveness and the facility to have tumor recurrences, the difficulty to reach tumor and drugs resistance.

Therefore, the identification of new effective agents, used also in combination with surgery, represent a necessary medical treatment to improve the war against GB.

MM is a hematologic neoplastic disorder characterized by an abnormal proliferation of monoclonal plasma cells in bone marrow. Its spread has remained fairly stable over time with 30,770 newly diagnosed cases annually in USA (46.7% female, 53.3% male). Genetic and environmental factors are correlated to the beginning of this disease and the progression is due to different microenvironment bone marrow changes as angiogenesis increase, immune response suppression, and bone resorption increase.

MM patients often show the typical CRAB criteria: hyperCalcaemia, Renal failure, Anaemia, Bone lesions. Unfortunately, patients in early stages of the pathology have no concerning signs or symptoms and therefore the diagnosis is confirmed to late. The diagnosis of MM can be performed through serum total protein levels, globulins, albumins level and plasma viscosity. The first-choice treatment is chemotherapy including melphalan, prednisone, cyclophosphamide, vincristine, doxorubicin. Recently other drugs have been evaluated for MM therapy as lenalidomide, pomalidomide, dexamethasone and thalidomide. Monoclonal antibodies and innovative target, as proteasome, are also investigate and new boronic proteasome inhibitors (bortezomib, carfilzomib, ixazomib) has been demonstrated as promising efficacy drugs against MM even though they present neurological side effects. Radiation therapy can also be used in MM treatment, while surgery is reserved to remove solitary plasmacytoma or in case of compression of the vertebral column which causes paralysis or excessive weakness. Nowadays a concrete cure is still missing, providing alternative therapies are necessary.

PC is one of the most lethal tumors with no prognosis improvement over the past 20-years. The age-standardized rate (ASR) incidence was highest in Europe, North America and Oceania (respectively 7.7 per 100,000 people, 7.6 per 100,000 people and 6.4 per 100,000 people). Incidence and mortality of PC is correlated with increasing age and is slightly more common in men than in women. The incidence is estimated to increase and will include 355,317 new cases within 2040. The etiology of PC has been extensively studied and the several risk factors have been identified and divided in modifiable (such as smoking, obesity, alcohol etc.) and non-modifiable factors (such as diabetes mellitus, genetic factors, infection etc.). In recent years, pre-existing chronic pancreatitis (due to alcohol abuse or hereditary factors), represents a strong risk factors of PC.

In the early stage of the pathology, PC is usually clinically silent, and patients show non-specific symptoms during the disease advance. Among the different non-specific symptoms, the signs of an obstruction within the biliary tree (such as abdominal pain, jaundice, pruritus, dark urine and acholic), anorexia, dyspnea and depression are very common. Depending on the type and stage of PC, treatment options can include surgery, radiation, chemotherapy and immunotherapy. Surgery offers a low cure rate, and radiotherapy is usually used as post-surgical treatment. Regarding chemotherapy, combination therapies (such as gemcitabine with cisplatin, oxaliplatin and paclitaxel) shows promising benefits but several side effects are observed due to the no-specific treatment. Therefore, new alternative therapeutic options are essential to identify in order to improve the survival rate of patients and try to limit the typical phenomenon of chemoresistance.

Since chemotherapy was the first-choice treatment against tumors, founding new effective drugs represent an urgent need.

The publications WO2007054623A1, WO2007076055A1, WO2006074025A1 disclose compounds (see FIG. 1 of '623, pag. 185 and 191 of '055 and example I of '025 publication) useful for the treatment of cancer.

WO2019142126A1 discloses anticancer compounds based on 1-(phenylpropargylaminocarbonyl)-4-ethenylcarbonyl-piperazines (see examples 1 to 47).

SUMMARY OF THE INVENTION

The present invention relies with substituted vinyl piperazine-piperidine urea derivatives, in particular, with a compound having general formula (I) and salts or hydrates or co-crystals thereof:

(I)

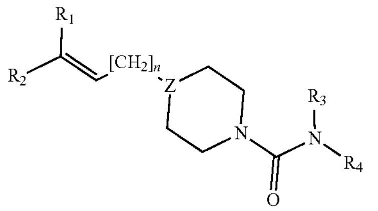

wherein:
Z is N or CH,
n is 1, 2, 3, 4 or 5,
$R_1$ is linear or branched C1-C3 alkyl,
$R_2$ and $R_4$ are independently a substituted or unsubstituted aryl or a substituted or unsubstituted cyclic moiety,
$R_3$ is hydrogen or linear or branched C1-C3 alkyl.

It has indeed surprisingly found that said compound of formula (I) is useful to prevent, treat and diagnose tumor diseases, in particular, among the other cancers, is highly effective active against glioblastoma (GB), multiple myeloma (MM).

It has indeed found that the substituted vinyl piperazine-piperidine urea derivatives, combining a substituted vinyl moiety with a piperazine urea or piperidine urea moiety, provides the effect of the invention, i.e. to be effective against cancers, and in particular, to be highly effective active against glioblastoma (GB), multiple myeloma (MM).

Therefore, the present invention related to promising anticancer substituted vinyl piperazine-piperidine urea derivatives of formula (I), described above, or salts, hydrates or co-crystals thereof.

Another aspect is a process for the preparation of the compound of formula (I),

A third aspect of the present invention are pharmaceutical compositions comprising a substituted vinyl piperazine-piperidine urea derivative of formula (I) or an addition salt thereof with pharmaceutically acceptable organic and inorganic acids, and at least one pharmaceutically acceptable excipient.

Finally, another aspect is the compound of formula (I) or pharmaceutical compositions thereof, for use in medicine, in particular, for use in method of treatments of cancer, i.e. for use as anticancer agents, more in particular, for use in the treatment of glioblastoma (GB) or multiple myeloma (MM).

DETAILED DESCRIPTION OF THE INVENTION

Figure 1:
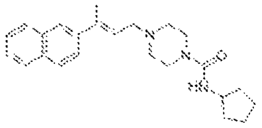
FIGS. 1 and 2 represent, respectively, the $^1H$ NMR and $^{13}C$ NMR of compound 26.
Figure 1:
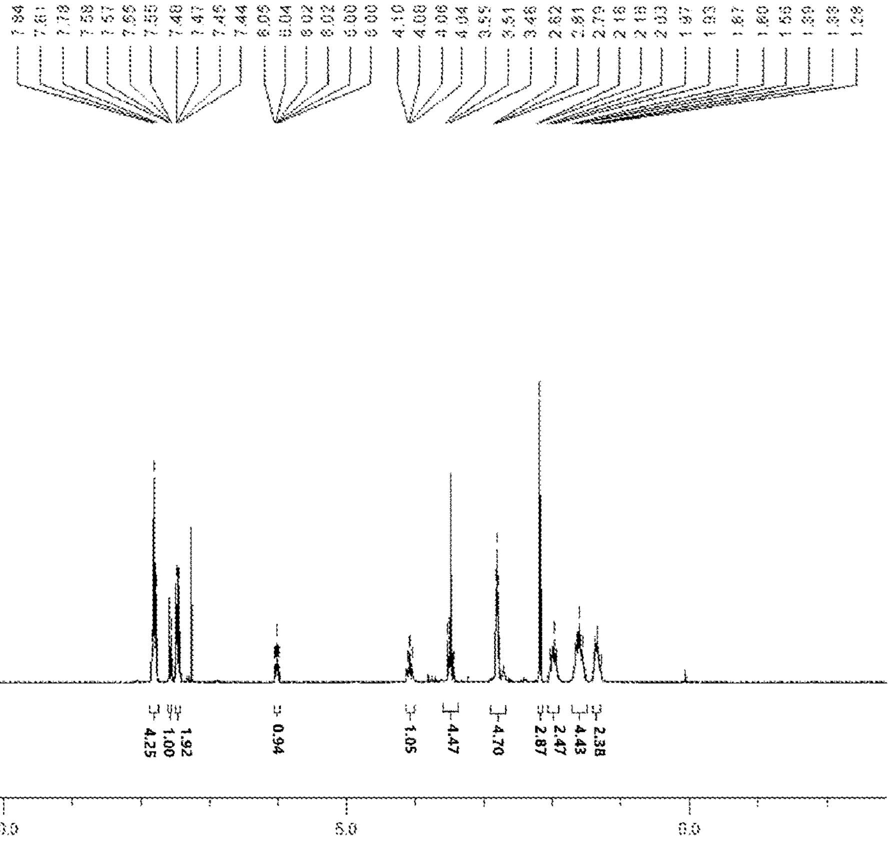
Figure 2:
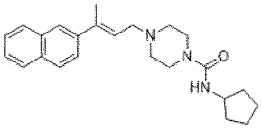
Figure 2:
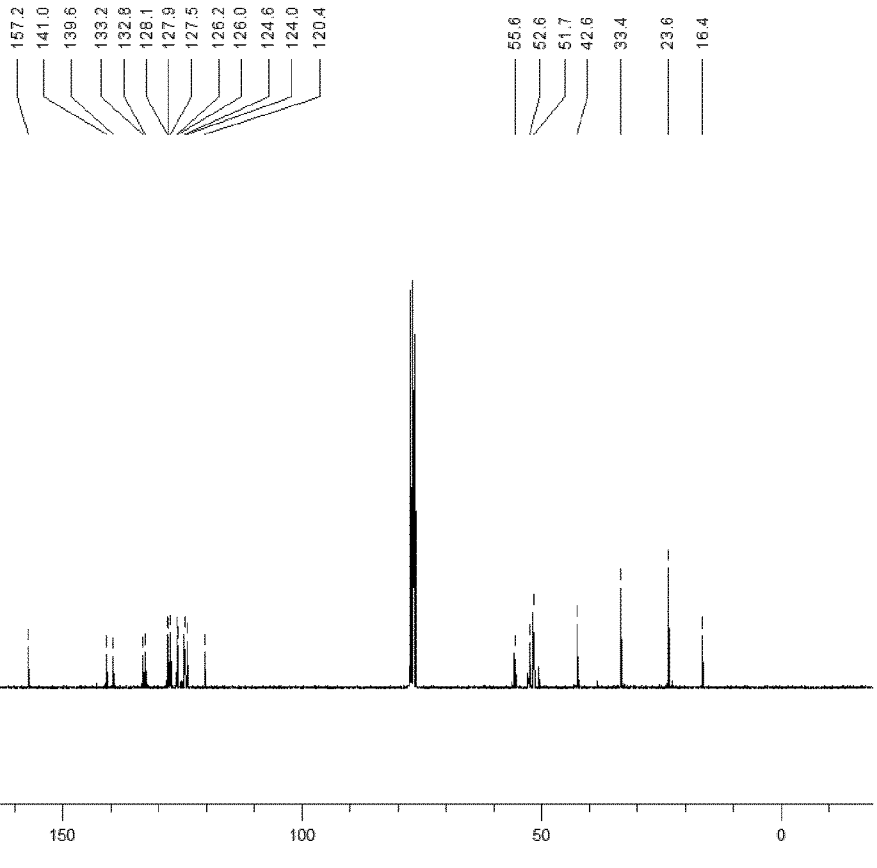
Figure 3:
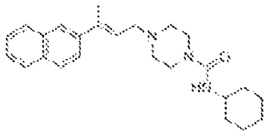
FIGS. 3 and 4 represent, respectively, the $^1H$ NMR and $^{13}C$ NMR of compound 27
Figure 3:
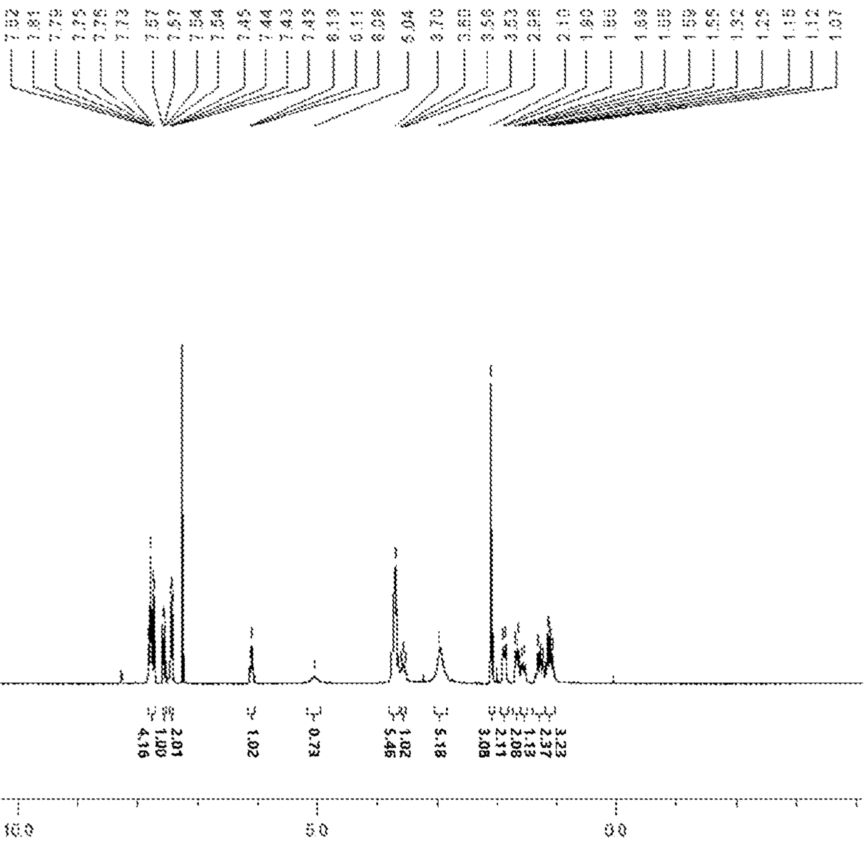
Figure 4:
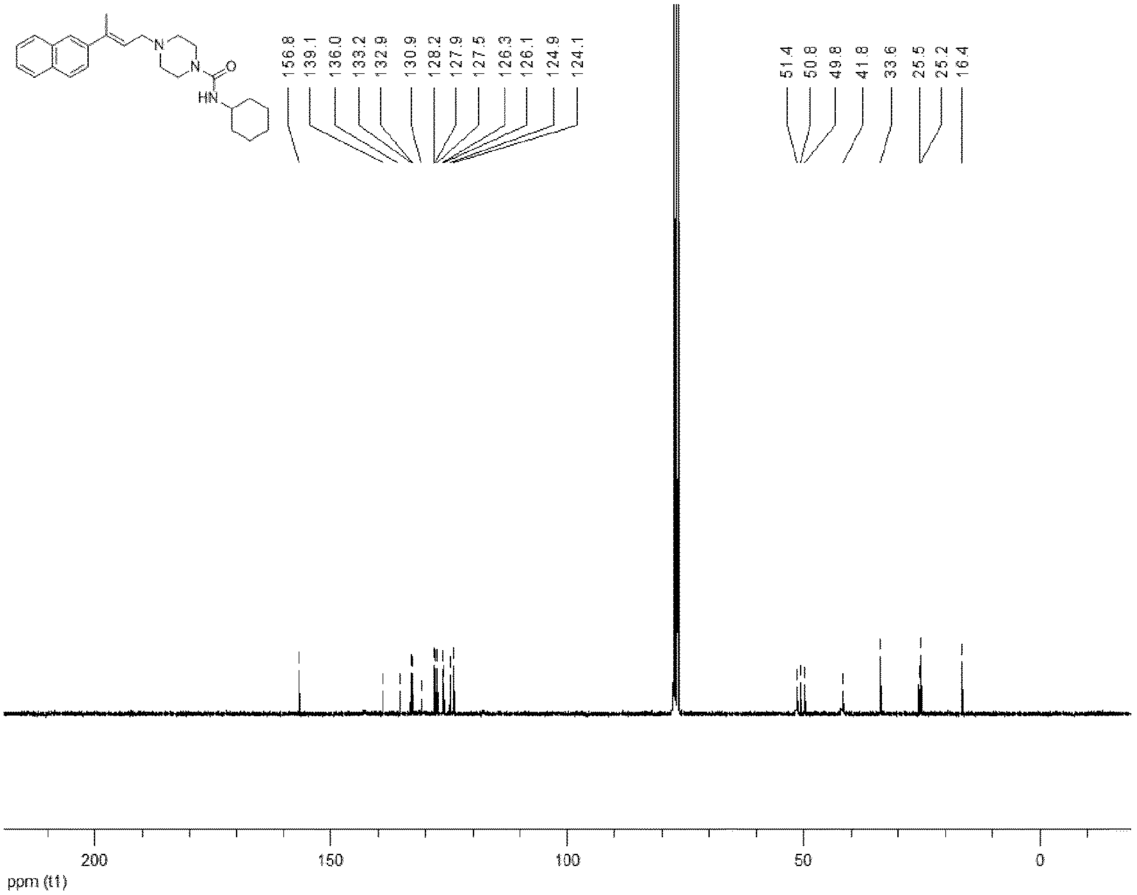
Figure 5:
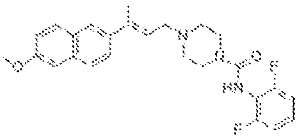
FIGS. 5 and 6 represent, respectively, the $^1H$ NMR and $^{13}C$ NMR of compound 30.
Figure 5:
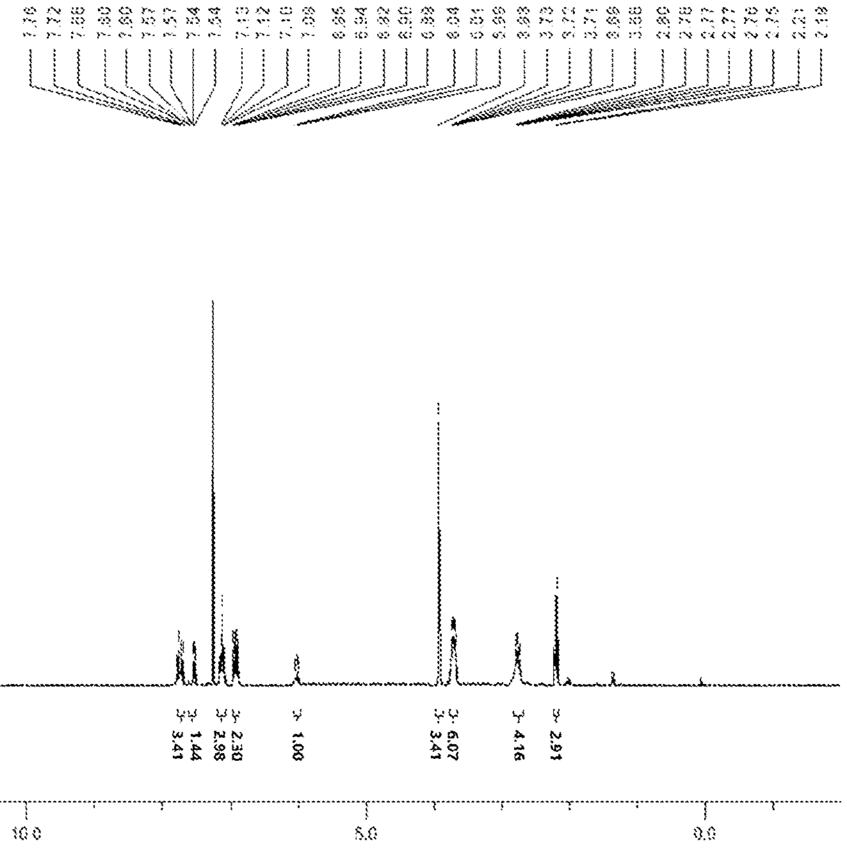
Figure 6:
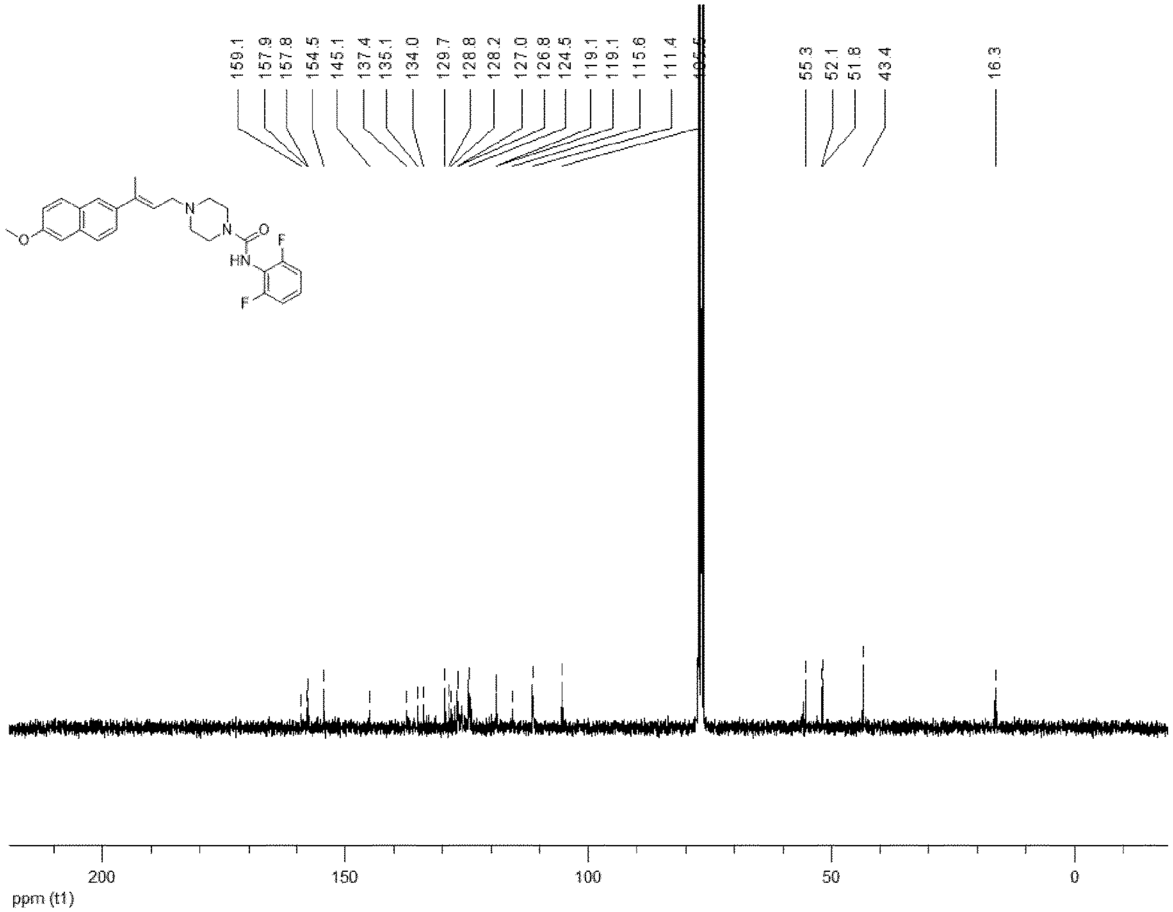

An object of the present invention is a compound of formula (I) and salts or hydrates or co-crystals thereof:

(I)

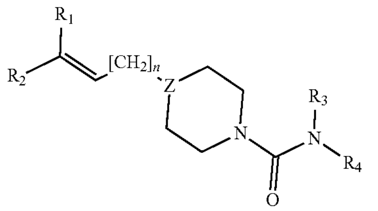

wherein:
Z is N or CH,
n is 1, 2, 3, 4 or 5,
$R_1$ is linear or branched C1-C3 alkyl,
$R_2$ and $R_4$ are independently a substituted or unsubstituted aryl or a substituted or unsubstituted cyclic moiety,
$R_3$ is hydrogen or linear or branched C1-C3 alkyl.

As said above, it has indeed surprisingly found, that the combination of a substituted vinyl moiety with a piperazine urea or with piperidine urea moiety, provides the effect of the substituted vinyl piperazine-piperidine urea compounds of formula (I) of the invention, i.e. to be effective against cancers, and in particular, to be highly effective active against glioblastoma (GB), multiple myeloma (MM). Specifically, the compound of formula (I) showed antitumor activity towards cell lines, among them RPMI-8226, U87 and Panc-1 human cell lines inducing morphology changing, decreasing number of vital-cell and triggering apoptosis events (see experimental part for details).

In the compound of formula (I), Z can be nitrogen N or CH, thus, providing respectively a piperazine or a piperidine ring, and therefore, a piperazine or a piperidine compound.

According to a preferred embodiment, Z is N, thus piperazine ring compound (1) is preferred.

In the compound of formula (I), n is an integer number, comprised between 1 and 5. Therefore n can be 1, 2, 3, 4, or 5. According to a preferred embodiment, n is 1, 2 or 3, more preferably n is 1 or 2, and again more preferably n is 1.

In the compound of formula (I), $R_3$ can be hydrogen or linear or branched C1-C3 alkyl, i.e. can be methyl, ethyl, n-propyl or isopropyl. According to a preferred embodiment, $R_3$ is hydrogen.

In the compound of formula (I), $R_1$ together with $R_2$ provides the substitution of the vinyl function, thus providing the part of the name of "substituted vinyl" to the compound of formula (I).

In the compound of formula (I), $R_1$ is a linear or branched C1-C3 alkyl, i.e. can be methyl, ethyl, n-propyl or isopropyl. According to a preferred embodiment, $R_1$ is methyl.

In the compound of formula (I), $R_2$ and $R_4$ are independently a substituted or unsubstituted aryl or a substituted or unsubstituted cyclic moiety.

It has to be clear that $R_2$ and $R_4$ can be equal or different each other. The term independently means that $R_2$ and $R_4$ can have any meaning so that they can or different.

In the present description and in the claims that follow, the term "aryl or cyclic moiety" for $R_2$ and $R_4$ means, for example, phenyl, 3-methoxyphenyl, naphthyl, 4-methoxynaphthyil, trifluoromethylphenyl, p-tolyl, 2,6-difluorophenyl, 3,5-difluorophenyl, 4-(trifluoromethyl)phenyl, 3-fluorophenyl, 3-chlorophenyl, 2,4-methoxyphenyl, 3,5-methoxynaphthyl, 3,5-methoxyphenyl and 4,6-methoxynaphthyl, 5-methoxyphenyl, 6-methoxynaphthyl, cyclohexane, cyclopentane and decahydronaphthalene.

In the compound of formula (I), $R_2$ and $R_4$ can be a substituted or unsubstituted aryl, such as, phenyl, naphthyl, biphenyl or binaphthyl derivates, etc.

Furthermore, $R_2$ and $R_4$ can be a substituted or unsubstituted cyclic moiety, such as five or six member rings derivatized (alone or condensate), substituted or substituted C3-C12 cycloalkyl, etc.

According to a preferred embodiment, in the compound of formula (I), $R_4$ is substituted or unsubstituted C5-C6 cycloalkyl or is substituted or unsubstituted phenyl. More preferably, $R_4$ is unsubstituted cyclopentyl, unsubstituted cyclohexyl, phenyl, 4-methylphenyl, 2,6-difluorophenyl, or 4-trifluoromethylphenyl.

According to a preferred embodiment of the invention, $R_2$ is a substituted or unsubstituted aryl.

According to a more preferred embodiment $R_2$ is substituted or unsubstituted phenyl or substituted or unsubstituted napthyl, thus providing vinylnaphtalen piperazine-piperidine urea derivatives of the invention. Again more preferably, $R_2$ is substituted or unsubstituted 2-napthyl, thus providing vinyl-2-naphtalen piperazine-piperidine urea derivatives of the invention.

In particular, for compound of formula (I), $R_2$ is substituted or unsubstituted 2-napthyl having the following formula (II):

(II)

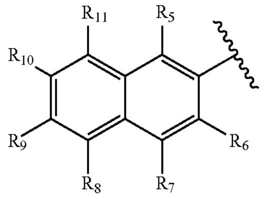

wherein, $R_5$, $R_6$, $R_7$, $R_8$, $R_9$, $R_{10}$, $R_{11}$, are independently hydrogen, linear or branched C1-C4 alkyl, linear or branched C1-C4 alcoxy or halogen.

According to a preferred embodiment, in the compound of formula (I), with reference to naphyl (II), $R_5$, $R_6$, $R_7$, $R_8$, $R_{10}$, $R_{11}$, are hydrogen and $R_9$ is hydrogen, fluorine, chlorine or methoxy.

Therefore, according to a preferred embodiment of the invention, $R_2$ is a substituted or unsubstituted aryl and $R_4$ is substituted or unsubstituted C3-C12 cycloalkyl. More preferably, $R_2$ is a substituted or unsubstituted naphtyl and $R_4$ is substituted or unsubstituted C5-C6 cycloalkyl or is substituted or unsubstituted phenyl. Again more preferably, $R_2$ is a substituted or unsubstituted 2-naphtyl and $R_4$ is unsubstituted cyclopentyl, unsubstituted cyclohexyl, phenyl, 4-methylphenyl, 2,6-difluorophenyl, or 4-trifluoromethylphenyl.

According to an again more preferred embodiment, in the compound of formula (I), with reference to naphyl (II), $R_5$, $R_6$, $R_7$, $R_8$, $R_{10}$, $R_{11}$, are hydrogen and $R_9$ is hydrogen, fluorine or methoxy and $R_4$ is unsubstituted cyclopentyl, unsubstituted cyclohexyl, phenyl, 4-methylphenyl, 2,6-difluorophenyl, or 4-trifluoromethylphenyl.

Therefore, the following compound included in the scope of compound of formula (I), are particularly preferred:

(E)-4-(3-(6-fluoronaphthalen-2-yl)pent-2-en-1-yl)-N-(4-fluorophenyl)piperazine-1-carboxamide, (E)-N-(3,5-difluorophenyl)-4-(3-(6-methoxynaphthalen-2-yl)pent-2-en-1-yl)piperidine-1-carboxamide, (E)-N-cyclohexyl-4-(3-(6-fluoronaphthalen-2-yl)pent-2-en-1-yl)piperidine-1-carboxamide, (E)-4-(3-(naphthalen-2-yl)but-2-en-1-yl)-N-phenylpiperazine-1-carboxamide, (E)-4-(3-(naphthalen-2-yl)but-2-en-1-yl)-N-(4-(trifluoromethyl)phenyl)piperazine-1-carboxamide, (E)-N-cyclopentyl-4-(3-(naphthalen-2-yl)but-2-en-1-yl)piperazine-1-carboxamide, (E)-N-cyclohexyl-4-(3-(naphthalen-2-yl)but-2-en-1-yl)piperazine-1-carboxamide, (E)-4-(3-(naphthalen-2-yl)but-2-en-1-yl)-N-(p-tolyl)piperazine-1-carboxamide, (E)-4-(3-(6-methoxynaphthalen-2-yl)but-2-en-1-yl)-N-(4-(trifluoromethyl)phenyl)piperazine-1-carboxamide, (E)-N-(2,6-difluorophenyl)-4-(3-(6-methoxynaphthalen-2-yl)but-2-en-1-yl)piperazine-1-carboxamide.

(E)-4-(4-(6-methoxynaphthalen-2-yl)pent-3-en-1-yl)-N-(4-(trifluoromethyl)phenyl)piperazine-1-carboxamide, (E)-4-(4-(6-methoxynaphthalen-2-yl)pent-3-en-1-yl)-N-phenylpiperazine-1-carboxamide.

The salts or hydrates or co-crystals of the compound of formula (I) are also effective in the treatment of cancer. According to a preferred embodiment, salts are formed with pharmaceutically acceptable inorganic and organic acids. In particular, the compounds of formula (I) that are useful according to the present invention are preferably used as addition salts with pharmaceutically acceptable organic or inorganic acids. Preferably, the pharmaceutically acceptable organic acids are selected from the group consisting of oxalic acid, maleic acid, methanesulfonic acid, para-toluenesulfonic acid, succinic acid, chloridric acid, malic acid and tartaric acid. Preferably, the pharmaceutically acceptable inorganic acids are selected from the group consisting of hydrochloric acid, hydrobromic acid, phosphoric acid and sulfuric acid. Hydrates are complex of the compound (I) with one or more water molecules. Co-crystals are solid complex of the compound of formula (I) with one or more other compounds (co-formers) which can be solvents or any compound able to provide complexes with the compound of formula (I).

Process for the preparation of the compound of formula (I) as described above:

(I)

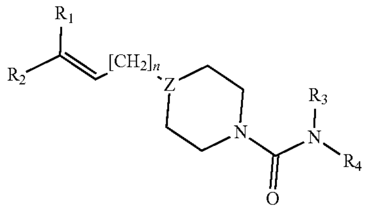

comprising the reaction of the compound (A):

(A)

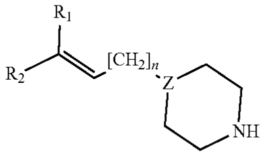

with the compound of formula (B):

(B)

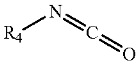

wherein n, Z, $R_1$, $R_2$, $R_3$ and $R_4$ have the same meaning of the compound of formula (I). This process applies to any one preferred embodiments above mentioned with reference to the compound (I).

For the preparation of the compound (A), said compound can be prepared by N-deprotection reaction of the compound of formula (A-1):

(A-1)

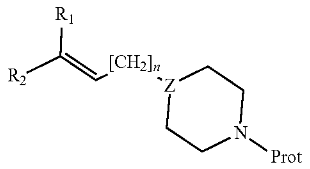

wherein Prot is a nitrogen protecting group.

The nitrogen protecting group Prot includes, among the others, Boc, Fmoc, Z, etc., being Boc the preferred nitrogen protecting group. Boc means tert-butylossicarbonil.

The compound of formula (A-1) can be prepared by coupling reaction of the compound (A-2) or of the compound (A-3) with the compound (A-4):

(A-2)

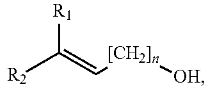

(A-3)

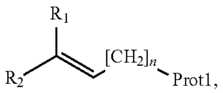

(A-4)

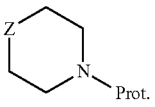

wherein Prot is a nitrogen protecting group and Prot 1 is a hydroxyl protecting group.

The hydroxyl protecting group Prot1 includes, among the other, Mesyl, Tosyl, etc., being Mesyl the preferred hydroxyl protecting group.

According to a preferred embodiment of the process for the preparation of the compound of formula (I) Prot1 hydroxyl protecting group is Mesyl group.

According to a preferred embodiment of the process for the preparation of the compound of formula (I) the Prot nitrogen protecting group is Boc.

According to more a preferred embodiment of the process for the preparation of the compound of formula (I) the Prot nitrogen protecting group is Boc and hydroxyl protecting group Prot1 is mesyl.

Another object are pharmaceutical compositions comprising the compound of formula (I) or salts or hydrates or co-crystals thereof and at least one pharmaceutically acceptable excipient.

Indeed, typically, the substituted vinyl piperazine-piperidine urea compounds of formula (I) are administered in the form of a pharmaceutical composition.

Preferably, the pharmaceutical composition according to the present invention is prepared in suitable dosage forms comprising an effective amount of the compound of formula (I) or a pharmaceutically acceptable acid-addition salt thereof, and at least one pharmaceutically acceptable excipient.

Examples of suitable dosage forms are tablets, coated tablets, capsules, granules, powders, solutions, suspensions, emulsions, syrups, drops and chewing gums for oral administration; solutions, creams, gels, pastes and ointments for topical administration; medicated patches for transdermal administration; suppositories for rectal administration; and injectable sterile solutions.

Examples of pharmaceutically acceptable excipients are, for example, diluents, binders, glidants, disintegrants, preservatives, stabilizers, buffers, surfactants, solubilizers, salts for regulating the osmotic pressure, emulsifiers, sweeteners, colorants, flavourings and the like.

The amount of the substituted vinyl piperazine-piperidine urea derivatives of formula (I) or the pharmaceutically acceptable acid-addition salts thereof in the pharmaceutical composition according to the present invention may vary on the basis of factors such as, for example, the type of pathology to be treated, the seriousness of the complaint, the weight of the patient, the dosage form, the selected route of administration, the number of administrations per day and the efficacy of the substituted vinyl piperazine-piperidine urea compounds of formula (I). However, a person skilled in the art can determine the optimum amount of the different derivatives of formula (I) that are useful according to the present invention in a simple and routine manner.

Suitable dosage forms for administering the compounds that are useful according to the present invention may be prepared, via techniques known in the art and comprise mixing, granulation, compression, dissolution, sterilization and the like.

Another aspect is the compound of formula (I) or salts or hydrates or co-crystals or pharmaceutical compositions thereof for use in medicine.

Particularly, the compound of formula (I) or salts or hydrates or co-crystals or pharmaceutical compositions are suitable for use in a method of prevention or treatment or diagnosis of cancer.

More particularly the compound of formula (I) is for use in the prevention, treatment or diagnosis of cancer diseases. The compound of formula (I) or salts or hydrates or co-crystals or pharmaceutical compositions can be used as anticancer agents.

According to a preferred embodiment, the compound of formula (I) or salts or hydrates or co-crystals or pharmaceutical compositions are for use in a method of treatment of cancer, wherein cancer is glioblastoma (GB), multiple myeloma (MM) or pancreatic cancer (PC).

Preferably, the abovementioned compounds of formula (I) are for use in the diagnosis of cancer, more preferably glioblastoma, multiple myeloma or pancreatic cancer.

Advantageously, for the diagnosis of cancer, the abovementioned compounds of formula (I) are marked with radioactive isotopes with short half-lives, for example carbon-11 (11C), nitrogen-13 (13N), or oxygen-15 (15O).

Methods for the diagnosis of cancer using compounds labelled with radioactive isotopes are known to those skilled in the art and comprise, for example, positron emission tomography (PET).

Non-limiting examples of the compounds of formula (I) that are useful according to the present invention are represented in Table 1 below.

TABLE 1

| No. | IUPAC name | Structure |
|---|---|---|
| 1 | (E)-4-(3-(4-chlorophenyl)pent-2-en-1-yl)-N-cyclohexylpiperazine-1-carboxamide | 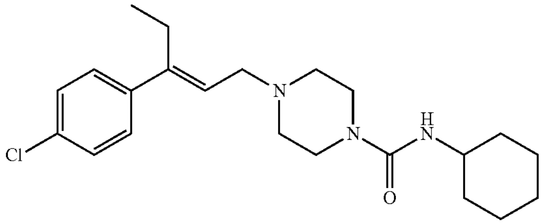 [SMILES: CC/C(=C\CN1CCN(C(=O)NC2CCCCC2)CC1)c1ccc(Cl)cc1] |
| 2 | (E)-N-cyclohexyl-4-(3-phenylbut-2-en-1-yl)piperazine-1-carboxamide | 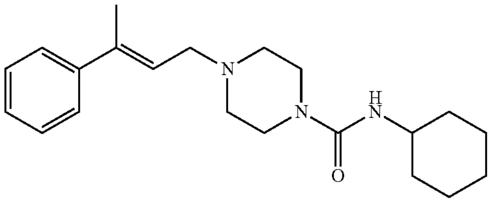 [SMILES: C/C(=C\CN1CCN(C(=O)NC2CCCCC2)CC1)c1ccccc1] |
| 3 | (E)-4-(3-(4-methoxyphenyl)pent-2-en-1-yl)-N-phenylpiperidine-1-carboxamide | 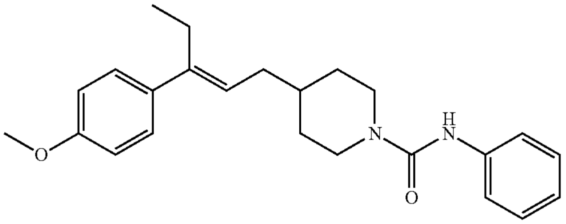 [SMILES: CC/C(=C\CC1CCN(C(=O)Nc2ccccc2)CC1)c1ccc(OC)cc1] |
| 4 | (E)-4-(4-phenylpent-3-en-1-yl)-N-(4-(trifluoromethyl)phenyl)piperazine-1-carboxamide | 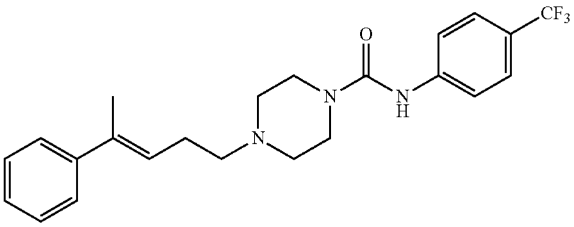 [SMILES: C/C(=C\CCN1CCN(C(=O)Nc2ccc(C(F)(F)F)cc2)CC1)c1ccccc1] |
| 5 | (E)-N-phenyl-4-(4-phenylpent-3-en-1-yl)piperazine-1-carboxamide | 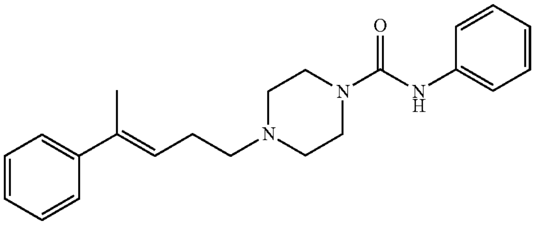 [SMILES: C/C(=C\CCN1CCN(C(=O)Nc2ccccc2)CC1)c1ccccc1] |
| 6 | (E)-4-(3-(4-chlorophenyl)but-2-en-1-yl)-N-(p-tolyl)piperazine-1-carboxamide | 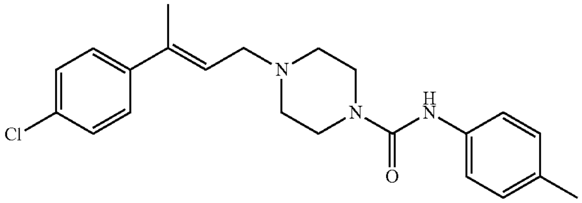 [SMILES: C/C(=C\CN1CCN(C(=O)Nc2ccc(C)cc2)CC1)c1ccc(Cl)cc1] |
| 7 | (E)-4-(3-([1,1'-biphenyl]-4-yl)pent-2-en-1-yl)-N-(4-(trifluoromethyl)phenyl)piperidine-1-carboxamide | 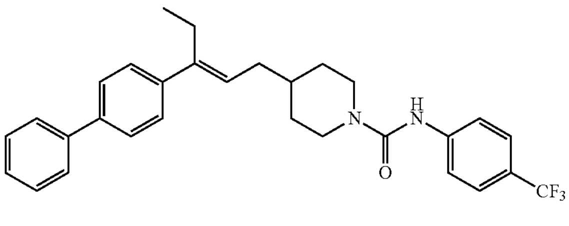 [SMILES: CC/C(=C\CC1CCN(C(=O)Nc2ccc(C(F)(F)F)cc2)CC1)c1ccc(-c2ccccc2)cc1] |

TABLE 1-continued

| No. | IUPAC name | Structure |
|---|---|---|
| 8 | (E)-4-(3-(6-chloronaphthalen-2-yl)pent-2-en-1-yl)-N-(4-fluorophenyl)piperazine-1-carboxamide | 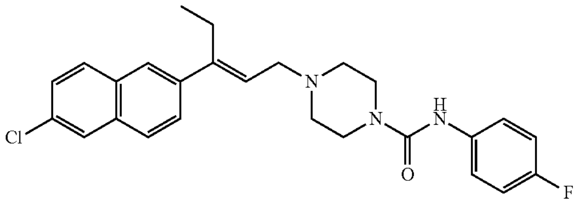 [SMILES: CC/C(=C\CN1CCN(C(=O)Nc2ccc(F)cc2)CC1)c1ccc2cc(Cl)ccc2c1] |
| 9 | (E)-4-(3-(4-methoxyphenyl)but-2-en-1-yl)-N-(p-tolyl)piperazine-1-carboxamide | 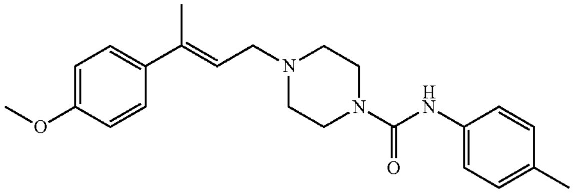 |
| 10 | (E)-4-(4-(6-methoxynaphthalen-2-yl)pent-3-en-1-yl)-N-(4-(trifluoromethyl)phenyl)piperazine-1-carboxamide | 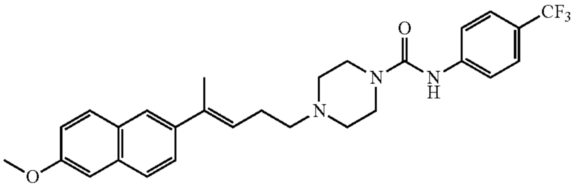 [SMILES: COc1ccc2cc(/C(C)=C/CCN3CCN(C(=O)Nc4ccc(C(F)(F)F)cc4)CC3)ccc2c1] |
| 11 | (E)-4-(4-(6-methoxynaphthalen-2-yl)pent-3-en-1-yl)-N-phenylpiperazine-1-carboxamide | 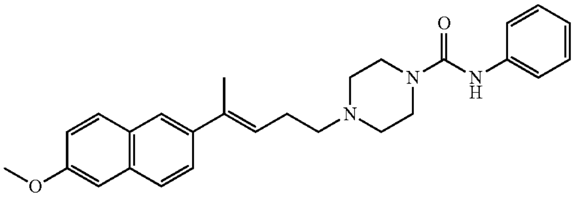 [SMILES: COc1ccc2cc(/C(C)=C/CCN3CCN(C(=O)Nc4ccccc4)CC3)ccc2c1] |
| 12 | (E)-4-(3-(4-chlorophenyl)but-2-en-1-yl)-N-cyclohexylpiperazine-1-carboxamide | 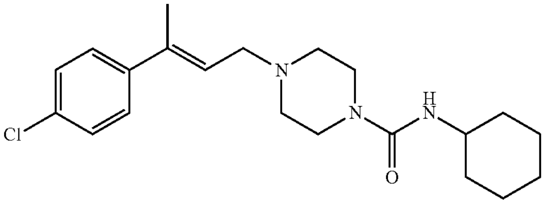 [SMILES: C/C(=C\CN1CCN(C(=O)NC2CCCCC2)CC1)c1ccc(Cl)cc1] |
| 13 | (E)-4-(3-(6-fluoronaphthalen-2-yl)pent-2-en-1-yl)-N-(4-fluorophenyl)piperazine-1-carboxamide | 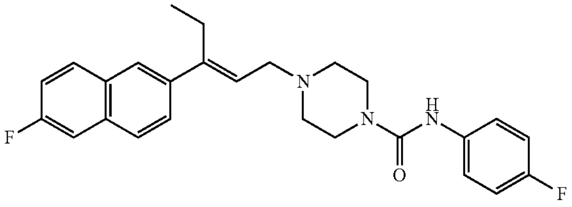 [SMILES: CC/C(=C\CN1CCN(C(=O)Nc2ccc(F)cc2)CC1)c1ccc2cc(F)ccc2c1] |
| 14 | (E)-N-(3,5-difluorophenyl)-4-(3-(6-methoxynaphthalen-2-yl)pent-2-en-1-yl)piperidine-1-carboxamide | 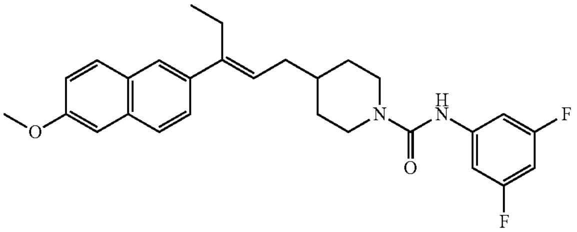 [SMILES: CC/C(=C\CC1CCN(C(=O)Nc2cc(F)cc(F)c2)CC1)c1ccc2cc(OC)ccc2c1] |

TABLE 1-continued

| No. | IUPAC name | Structure |
|---|---|---|
| 15 | (E)-N-cyclopentyl-4-(4-phenylpent-3-en-1-yl)piperazine-1-carboxamide | 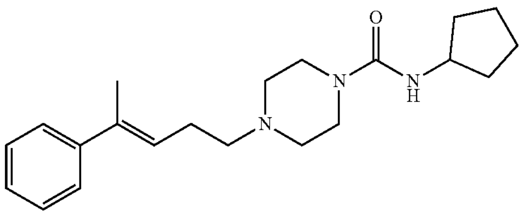 [SMILES: C/C(=C\CCN1CCN(C(=O)NC2CCCC2)CC1)c1ccccc1] |
| 16 | (E)-N-(2,4-difluorophenyl)-4-(4-(6-methoxynaphthalen-2-yl)pent-3-en-1-yl)piperazine-1-carboxamide | 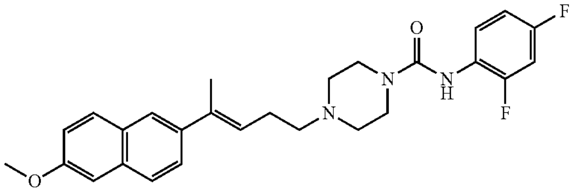 [SMILES: COc1ccc2cc(/C(C)=C/CCN3CCN(C(=O)Nc4ccc(F)cc4F)CC3)ccc2c1] |
| 17 | (E)-N-cyclohexyl-4-(3-(6-fluoronaphthalen-2-yl)pent-2-en-1-yl)piperidine-1-carboxamide | 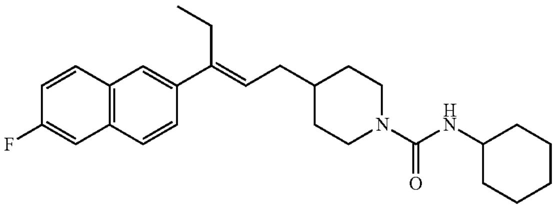 [SMILES: CC/C(=C\CC1CCN(C(=O)NC2CCCCC2)CC1)c1ccc2cc(F)ccc2c1] |
| 18 | (E)-4-(3-(naphthalen-2-yl)but-2-en-1-yl)-N-phenylpiperazine-1-carboxamide | 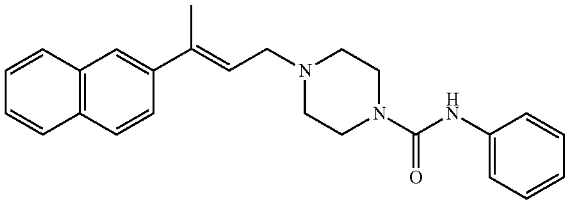 [SMILES: C/C(=C\CN1CCN(C(=O)Nc2ccccc2)CC1)c1ccc2ccccc2c1] |
| 19 | (E)-4-(3-(4-methoxyphenyl)but-2-en-1-yl)-N-phenylpiperazine-1-carboxamide | 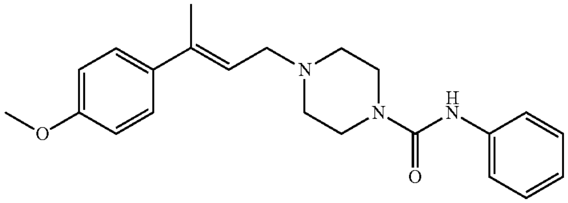 [SMILES: COc1ccc(/C(C)=C/CN2CCN(C(=O)Nc3ccccc3)CC2)cc1] |
| 20 | (E)-N-cyclopentyl-4-(3-(4-methoxyphenyl)pent-2-en-1-yl)piperidine-1-carboxamide | 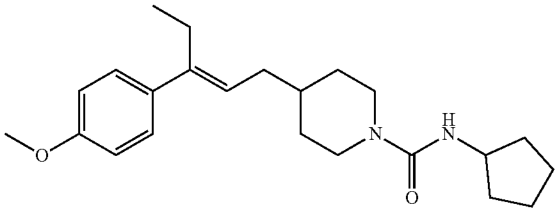 [SMILES: CC/C(=C\CC1CCN(C(=O)NC2CCCC2)CC1)c1ccc(OC)cc1] |
| 21 | (E)-N-cyclohexyl-4-(3-phenylbut-2-en-1-yl)piperazine-1-carboxamide | 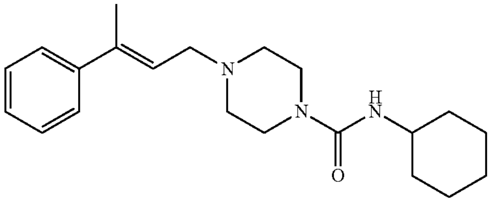 [SMILES: C/C(=C\CN1CCN(C(=O)NC2CCCCC2)CC1)c1ccccc1] |

TABLE 1-continued

| No. | IUPAC name | Structure |
|---|---|---|
| 22 | (E)-4-(3-(4-methoxyphenyl)but-2-en-1-yl)-N-(4-(trifluoromethyl)phenyl)piperazine-1-carboxamide | 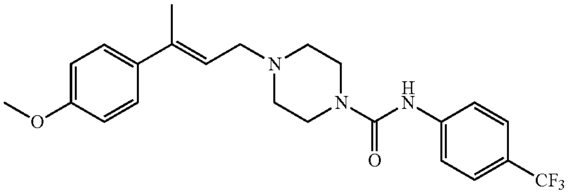 [SMILES: COc1ccc(/C(C)=C/CN2CCN(C(=O)Nc3ccc(C(F)(F)F)cc3)CC2)cc1] |
| 23 | (E)-N-cyclohexyl-4-(3-phenylbut-2-en-1-yl)piperidine-1-carboxamide | 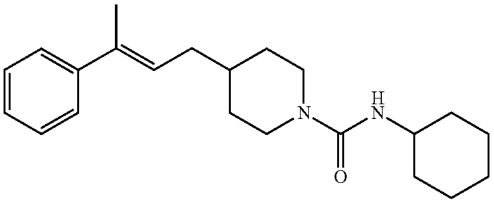 [SMILES: C/C(=C\CC1CCN(C(=O)NC2CCCCC2)CC1)c1ccccc1] |
| 24 | (E)-4-(3-(4-methoxyphenyl)but-2-en-1-yl)-N-(p-tolyl)piperidine-1-carboxamide | 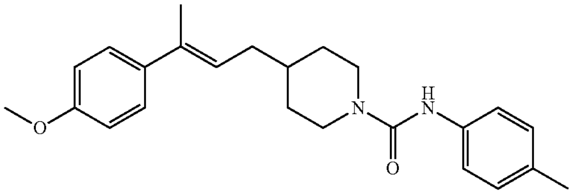 |
| 25 | (E)-4-(3-(naphthalen-2-yl)but-2-en-1-yl)-N-(4-(trifluoromethyl)phenyl)piperazine-1-carboxamide | 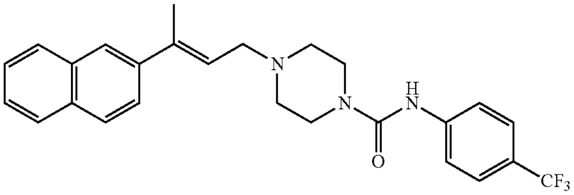 [SMILES: C/C(=C\CN1CCN(C(=O)Nc2ccc(C(F)(F)F)cc2)CC1)c1ccc2ccccc2c1] |
| 26 | (E)-N-cyclopentyl-4-(3-(naphthalen-2-yl)but-2-en-1-yl)piperazine-1-carboxamide | 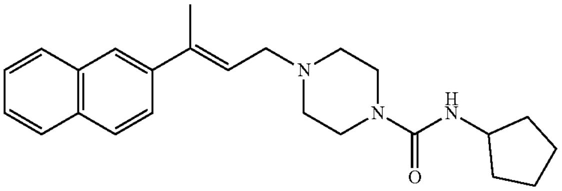 [SMILES: C/C(=C\CN1CCN(C(=O)NC2CCCC2)CC1)c1ccc2ccccc2c1] |
| 27 | (E)-N-cyclohexyl-4-(3-(naphthalen-2-yl)but-2-en-1-yl)piperazine-1-carboxamide | 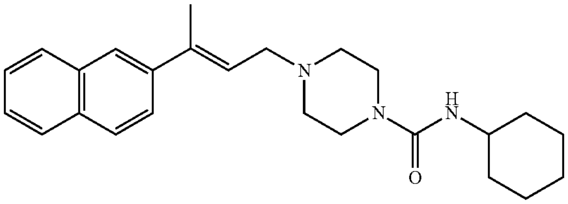 [SMILES: C/C(=C\CN1CCN(C(=O)NC2CCCCC2)CC1)c1ccc2ccccc2c1] |
| 28 | (E)-4-(3-(naphthalen-2-yl)but-2-en-1-yl)-N-(p-tolyl)piperazine-1-carboxamide | 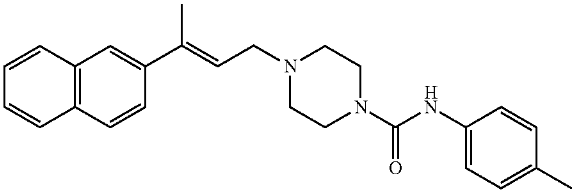 [SMILES: C/C(=C\CN1CCN(C(=O)Nc2ccc(C)cc2)CC1)c1ccc2ccccc2c1] |

TABLE 1-continued

| No. | IUPAC name | Structure |
|---|---|---|
| 29 | (E)-4-(3-(6-methoxynaphthalen-2-yl)but-2-en-1-yl)-N-(4-(trifluoromethyl)phenyl)piperazine-1-carboxamide | 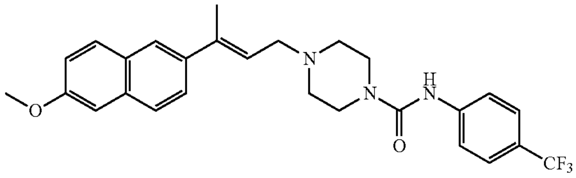 [SMILES: COc1ccc2cc(/C(C)=C/CN3CCN(C(=O)Nc4ccc(C(F)(F)F)cc4)CC3)ccc2c1] |
| 30 | (E)-N-(2,6-difluorophenyl)-4-(3-(6-methoxynaphthalen-2-yl)but-2-en-1-yl)piperazine-1-carboxamide | 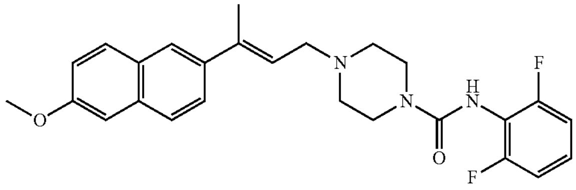 [SMILES: COc1ccc2cc(/C(C)=C/CN3CCN(C(=O)Nc4c(F)cccc4F)CC3)ccc2c1] |

The following examples are intended to illustrate the present invention without, however, limiting it in any way.

EXAMPLES

Among the various substituted vinyl piperazine-piperidine urea compounds, the piperazine urea derivatives are synthesized and tested in different cancer cell lines.

1. General Synthesis of the Compound Of Formula (I)

The compounds of formula (I) were prepared through the synthetic route explained below.

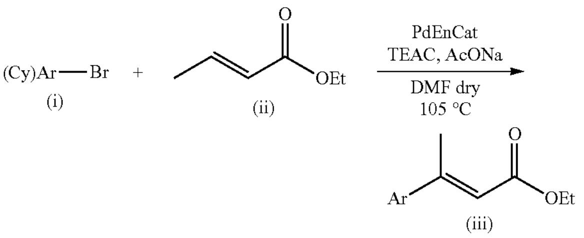

Step (a). Heck reaction was performed with aryl compounds (i) and ethyl crotonate (ii) through a palladium catalyst as palladium acetate microencapsulated in polyurea matrix (Pd EnCat®40), tetraethylammonium chloride (TEAC), a strong base, such as sodium acetate (NaOAc) and using N,N-dimethylformamide as solvent reaction. The reaction mixture, kept in inert medium and under magnetic stirring, is heated under reflux with an oil bath, obtaining the intermediate (iii).

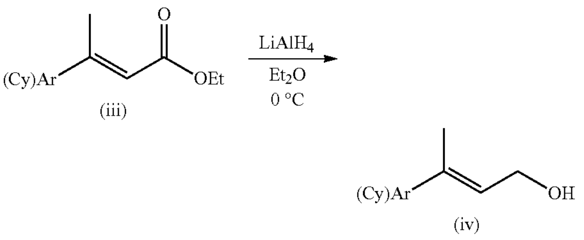

Step (b). The allylic ester (iii) was subjected to a reduction reaction by Lithium aluminum hydride ($LiAlH_4$) in a suitable solvent, for example, anhydrous diethyl ether ($Et_2O$) or tetrahydrofuran (THF). The reaction was performed in a 0 °C ice bath, until the intermediate of formula (iv) was obtained.

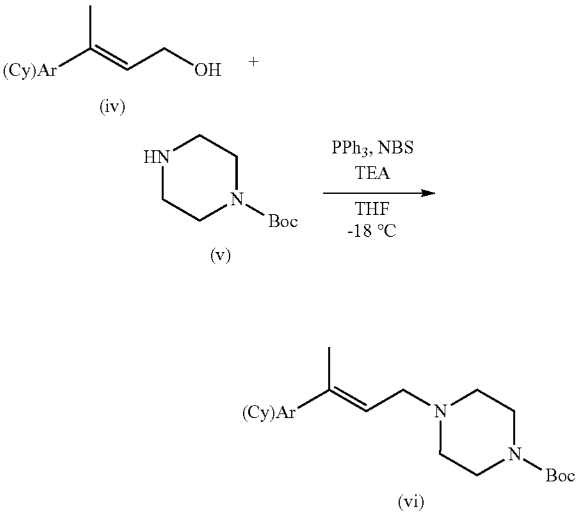

Step (c). The alcohol intermediate (iv) was subjected to a $S_N2$ reaction using the suitable solvent, for example anhydrous tetrahydrofuran (THF). Triphenylphosphine ($PPh_3$) and N-bromosuccinimide (NBS) were used to produce a reactive intermediate that, after the addition of intermediate (iv), and triethylamine (TEA) and N-Boc-piperazine (v), lead to the obtaining of intermediate of formula (vi).

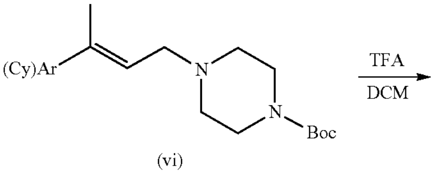

-continued

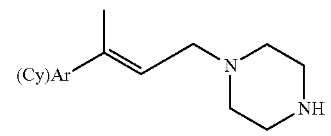

(vii)

Step (d). The deprotection of tert-butyloxycarbonyl group was performed using an acid, for example TFA, and the suitable solvent such as dichloromethane (DCM), thus the deprotected piperazine (intermediate (vii)) was obtained.

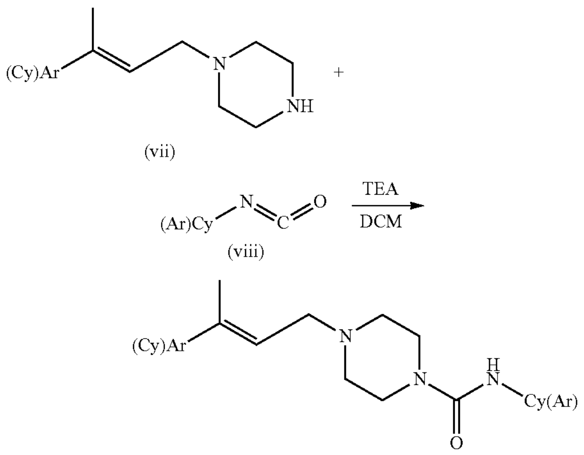

Step (e). The amine intermediate of formula (vii) was reacted with suitable isocyanate of formula (viii) in the presence of TEA and a suitable solvent, for example anhydrous DCM, until the desired compound of formula (II) was formed.

OR

The compounds of formula (I) were prepared through a sustainable synthetic route explained below.

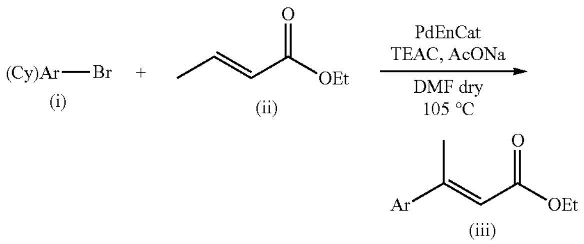

Step (a). Heck reaction was performed with aryl compounds (i) and ethyl crotonate (ii) through a palladium catalyst as palladium acetate microencapsulated in polyurea matrix (Pd EnCat®40), tetraethylammonium chloride (TEAC), a strong base, such as sodium acetate (NaOAc) and using N,N-dimethylformamide as solvent reaction. The reaction mixture, kept in inert medium and under magnetic stirring, is heated under MW, obtaining the intermediate (iii).

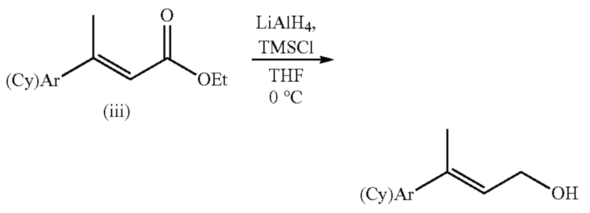

Step (b). The allylic ester (iii) was subjected to a reduction reaction by Lithium aluminum hydride ($LiAlH_4$) in a suitable solvent, for example, anhydrous diethyl ether ($Et_2O$) or tetrahydrofuran (THF). With the aim to reduce the amount of $LiAlH_4$, trimethylsilyl chloride was added. The reaction was performed in a 0 °C ice bath, until the intermediate of formula (iv) was obtained.

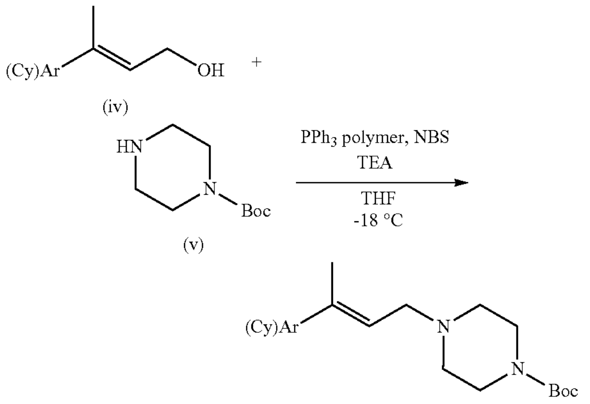

Step (c). The alcohol intermediate (iv) was subjected to a $S_N2$ reaction using the suitable solvent, for example anhydrous tetrahydrofuran (THF). Triphenylphosphine or triphenylphosphine supported by a polymer ($PPh_3$ polymer) and N-bromosuccinimide (NBS) were used to produce a reactive intermediate that, after the addition of intermediate (iv), and triethylamine (TEA) and N-Boc-piperazine (v), lead to the obtaining of intermediate of formula (vi).

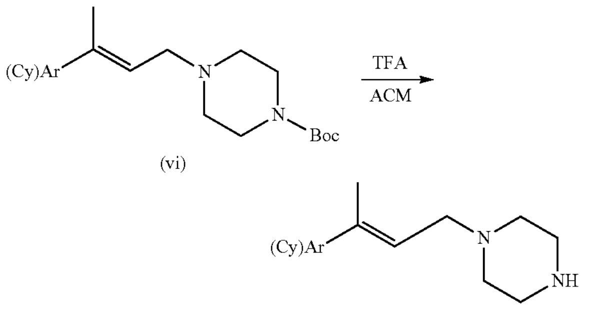

Step (d). The deprotection of tert-butyloxycarbonyl group was performed using an acid, for example TFA, and the suitable sustainable solvent such as acetonitrile (ACN), using MW assisted synthesis. Thus the deprotected piperazine (intermediate (vii)) was obtained.

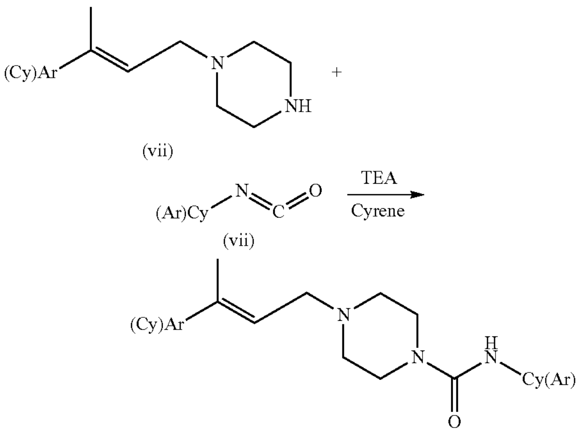

(vii) (vii) (II)

Step (e). The amine intermediate of formula (vii) was reacted with suitable isocyanate of formula (viii) in a sustainable solvent, for example Cyrene, until the desired compound of formula (II) was formed.

OR

The compounds of formula (I) characterized by a longer chain, for example $[CH]_n$ with n=3, were prepared through the synthetic route explained below.

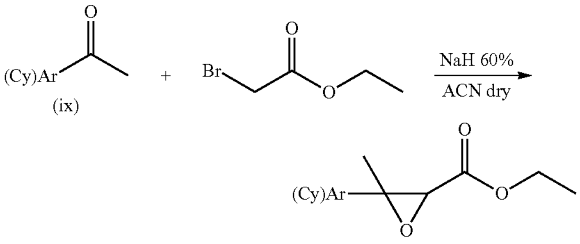

(ix) (x)

Step (a). Epoxide (x) was obtained by the addition of chiton and ethyl 2-bromoacetate from room temperature to 60 °C. The reaction mixture, kept in inert medium and under magnetic stirring, is heated under reflux with an oil bath, obtaining the intermediate (x).

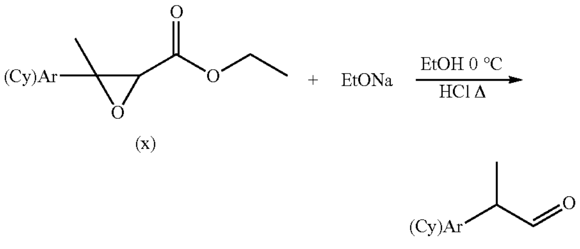

(x) (xi)

Step (b). The epoxide (x) was reacted with sodium ethoxide at 0 °C and subsequently added water to promote the hydrolyzation. The mixture was acidified and heated. After extraction with $Et_2O$, the intermediate xi was obtained without any purification.

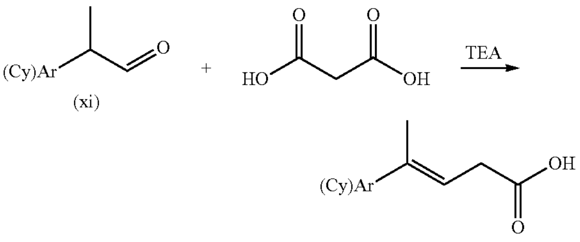

(xi) (xii)

Step (c). The Knoevenagel reaction was performed with aldehyde (xi) and malonic acid using TEA as solvent. The reaction mixture is heated under reflux with an oil bath, obtaining the intermediate (xii) after extraction ad work up and precipitation in acid water.

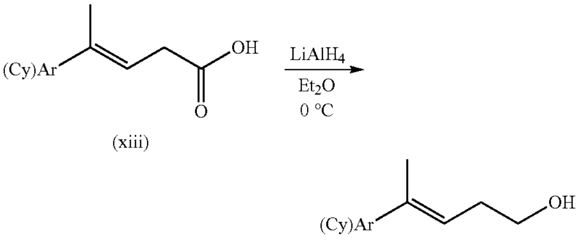

(xiii) (xiv)

Step (d). The intermediate (xii) was subjected to a reduction reaction by Lithium aluminum hydride ($LiAlH_4$) in a suitable solvent, for example, anhydrous diethyl ether ($Et_2O$) or tetrahydrofuran (THF). The reaction was performed in a 0 °C ice bath, until the intermediate of formula (xiii) was obtained.

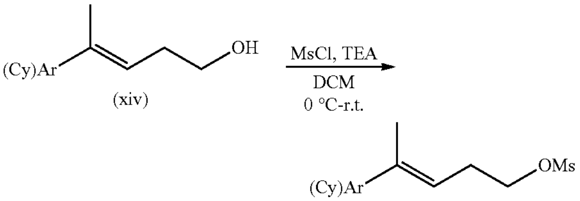

(xiv) (xv)

Step (e). Introduction of leaving group on compound (xv) was obtained reacting alcohol intermediate (xiv) with TEA and methanesulfonyl chloride (MsCl) or p-toluenesulfonyl chloride opportunely. The reaction, kept in inert medium and under magnetic stirring, was performed from 0 °C to room temperature.

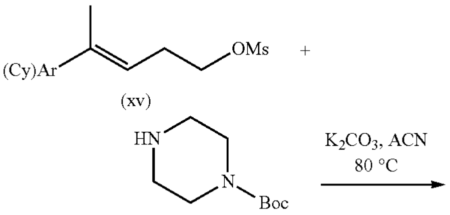

(xv) (v)

-continued

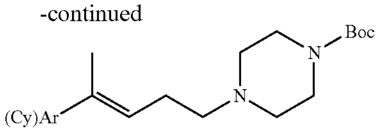

(xvi)

Step (f). The intermediate (xiv) was subjected to a $S_N2$ reaction using the suitable solvent, for example ACN. Boc-piperazine (v), $K_2CO_3$ were added, and the reaction mixture is heated under reflux with an oil bath.

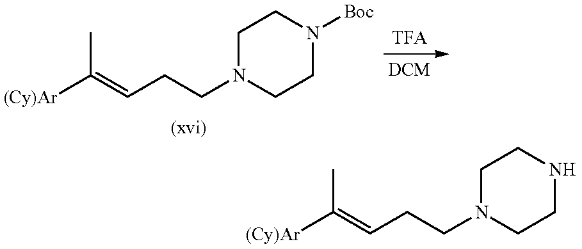

(xvi)

(xvii)

Step (g). The deprotection of tert-butyloxycarbonyl group was performed using an acid, for example TFA, and the suitable solvent such as dichloromethane (DCM), thus the deprotected piperazine was obtained.

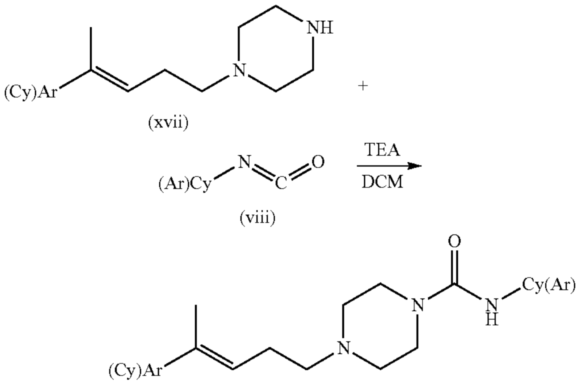

(xvii) + (viii)

(III)

Step (h). The amine intermediate of formula (xvii) was reacted with suitable isocyanate of formula (viii) in the presence of TEA and a suitable solvent, for example anhydrous DCM, until the desired compound of formula (III) was formed.

Synthesis of the Compounds of Formula (I)—Compounds 27-30

The compounds 26, 27, 28, 29 and 30 are prepared through the synthetic route described below.

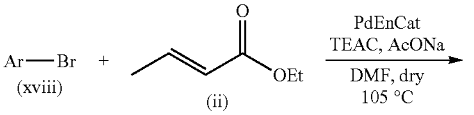

(xviii) + (ii)

-continued

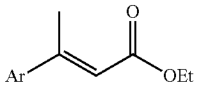

(xix)

Step (a). In a two-neck round-bottom flask, preserving the anhydrous conditions, solid reagents are added quickly. After sodium acetate (AcONa, 2 equiv.) addition, Palladium EnCat® (loading 0.4 mmol/g, 1%, 0.01 equiv.) is added with Tetraethylammonium chloride (TEAC, 2 equiv.). Afterwards, the liquid reagent (E)-ethyl but-2-enoate (1.5 equiv.; d=0.918 g/mL) and the dry solvent N,N-dimethylformamide (DMF) are added too.

Separately, in a round-bottom flask, a solution of aryl bromide (Ar—Br, 1 equiv.) in dry DMF is prepared. This solution is then transferred to a dropping funnel, obtaining a final concentration in the reaction ambient close to 0.35 M. This reaction mixture, kept in inert medium and under magnetic stirring, is heated under reflux with an oil bath until a temperature of 105 °C. After almost five hours the reaction has gone to completion. The reaction mixture is diluted and extracted three times with diethyl ether ($Et_2O$). The collected organic phases are washed with water, dried with sodium sulfate ($Na_2SO_4$) anhydrous, filtrated and evaporated to dryness at reduced pressure. The dark-brown raw oil obtained after solvent evaporation is purified by chromatography on silica gel in a yield of 55-60%.

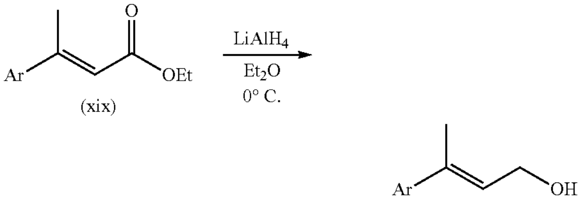

(xix)

(xx)

Step (b). In a one-neck round-bottom flask, preserving the anhydrous conditions, the allylic ester (1 equiv.) from the previous synthetic step is solubilized in dry $Et_2O$ under magnetic stirring. Once the solution is homogeneous, the reaction flask is put in a 0 °C ice bath. Afterwards, lithium aluminium hydride ($LiAlH_4$, 1 equiv., 1M solution in dry THF) is added, slowly and dropwise, to the reaction mixture. After 1 hour, the reaction is quenched by adding a few drops of ethyl acetate (AcOEt) and, afterwards, some of ammonium chloride ($NH_4Cl$) saturated aqueous solution. The workup procedure follows three extractions with $Et_2O$ and washing of the collected organic phases with Brine. After that, the organic phase is dried with anhydrous $Na_2SO_4$, filtrated and evaporated to dryness at reduced pressure. Depending on the purity of the raw product, as reported below, this is either purified by chromatography on silica gel or used directly in the subsequent reaction.

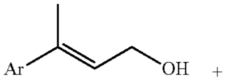

(xx) +

-continued

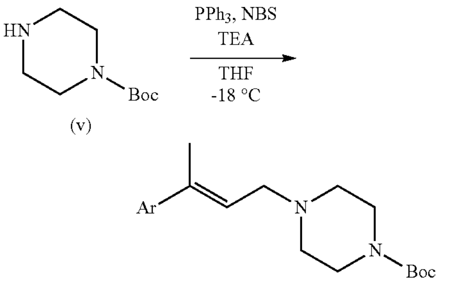

(v)

(xxi)

Step (c). In a one-neck round-bottom flask, a mixture of allylic alcohol (1 equiv.) and triphenylphosphine ($PPh_3$, 1.5 equiv.) is solubilized in dry THF under magnetic stirring, preserving the anhydrous conditions and in ice bath of −18 °C. The reaction mixture is treated with N-bromosuccinimide (NBS, 1.4 equiv.): this operation should be done carefully, adding the NBS portion-wise in six equal fractions each 5-10 minutes. Meanwhile, in another anhydrous round-bottom flask, the amines 1-Boc-piperazine (1.2 equiv.) and triethylamine (TEA, 2 equiv.) are solubilized in dry. This solution is later added to the reaction flask, previously cooled again to −18 °C. After the addition of these last reagents, the reaction flask is brought out from the ice bath one more time and let react overnight at room temperature under magnetic stirring. The raw product is worked up by dilution with $Et_2O$, filtration directly into the separating funnel and three times washing with a $Na_2CO_3$ saturated aqueous solution. The washed organic phase is then dried with $Na_2SO_4$ anhydrous, filtrated and evaporated to dryness at reduce pressure. This way a raw dark oil to be purified by chromatography on silica gel is obtained.

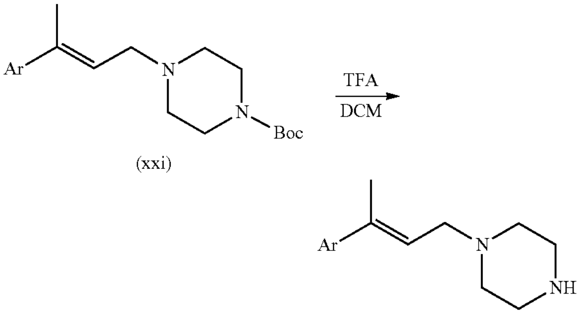

(xxi)

(xxii)

Step (d). Into a 2-necked round bottomed flask of the appropriate volume, the Boc-protected intermediate was dissolved in dichloromethane (DCM), and subsequently added trifluoroacetic acid (TFA, 10 equiv.) Solvent was evaporated and the resulting de-Boc products were used without further purification.

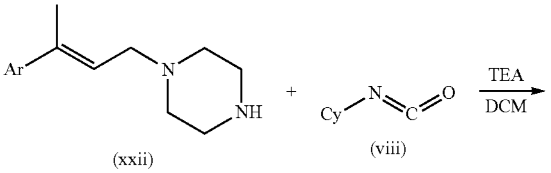

(xxii) (viii)

-continued

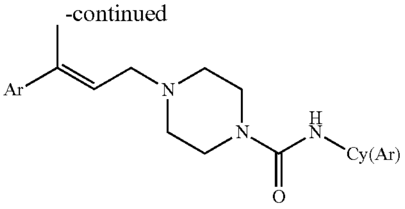

(IV)

Step (e). In a one-neck round-bottom flask, a mixture of triethylamine (TEA, 5 equiv.) and piperazine intermediate (1 equiv.) is solubilized in DCM under magnetic stirring. Then the corresponding isocyanates (1.5 eqiv.) were added. After 1-2 hour, the raw product was purified by chromatography on silica gel until the desired compound of formula (IV) was formed.

OR

The compounds 26, 27, 28, 29 and 30 are also prepared through a sustainable approach reducing the amount of solvent, replacing difficult-to-dispose reagents, modifying the purification procedure with precipitation, crystallization or used of derivatized resins. Moreover, air refrigerants were adopted for all reaction conducted on reflux condition.

The synthetic route described below.

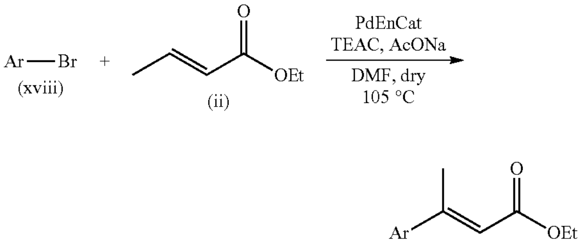

(xviii) (ii)

(xix)

Step (a). In a MW vessel, preserving the anhydrous conditions, solid reagents are added quickly. After sodium acetate (AcONa, 2 equiv.) addition, Palladium EnCat® (loading 0.4 mmol/g, 1%, 0.01 equiv.) is added with Tetraethylammonium chloride (TEAC, 2 equiv.). Afterwards, the aryl bromide (Ar—Br, 1 equiv.) the liquid reagent (E)-ethyl but-2-enoate (1.5 equiv.; d=0.918 g/mL) and the dry solvent N,N-dimethylformamide (DMF) are added too dropwise.

This reaction mixture, kept in inert medium and under magnetic stirring, is heated under MW assisted until a temperature of 120 °C, 2 min ramping, maximum pressure 250 psi, maximum potency 80 W for three cycles of 10 min each; thus the reaction has gone to completion. The reaction mixture is diluted and extracted three times with diethyl ether ($Et_2O$). The collected organic phases are washed with water, dried with sodium sulfate ($Na_2SO_4$) anhydrous, filtrated and evaporated to dryness at reduced pressure. The dark-brown raw oil obtained after solvent evaporation was purified through hexane precipitation. Thus, the crude was simplified to reduce the amount of solvent and silica gel for the subsequent chromatography. The intermediate (xi) was obtained with a yield of 55-60%.

A procedure to restore the Palladium EnCat® is performed, washing the powder with H2O and 2-propanol.

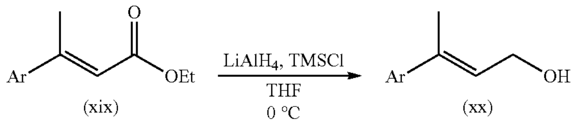

(xix) (xx)

Step (b). In a one-neck round-bottom flask, preserving the anhydrous conditions, the allylic ester (1 equiv.) from the previous synthetic step is solubilized in dry THF or $Et_2O$ under magnetic stirring. Once the solution is homogeneous, the reaction flask is put in a 0 °C ice bath. Afterwards, TMSC is added to active the carbonyl group and reduce the eq of lithium aluminum hydride. After 30 min lithium aluminum hydride ($LiAlH_4$, 0.7 equiv., 1M solution in dry THF) is added, slowly and dropwise, to the reaction mixture. After 1 hour, the reaction is quenched by adding a few drops of ethyl acetate (AcOEt) and, afterwards, some of ammonium chloride ($NH_4Cl$) saturated aqueous solution. The workup procedure follows three extractions with $Et_2O$ and washing of the collected organic phases with Brine. After that, the organic phase is dried with anhydrous $Na_2SO_4$, filtrated and evaporated to dryness at reduced pressure. After crystallization with cold heptane or hexane, the desired alcohol is obtained for the subsequent reaction.

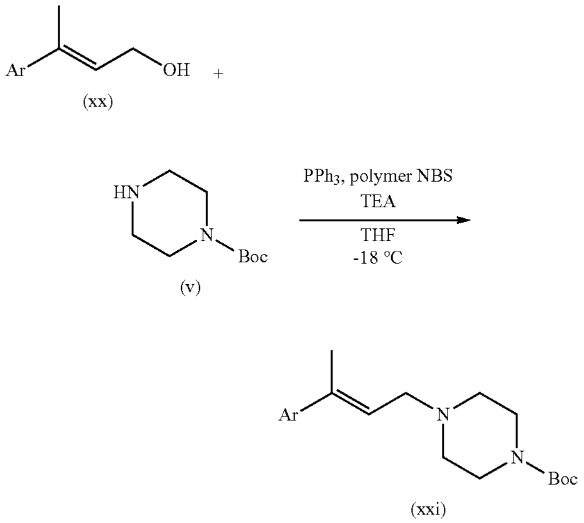

(xx) (v) (xxi)

Step (c). In a one-neck round-bottom flask, a mixture of allylic alcohol (1 equiv.) and triphenylphosphine ($PPh_3$, 1.5 equiv.) or triphenylphosphine polymer ($PPh_3$, 1.5 equiv., 3 mmol/g) is solubilized in dry THF under magnetic stirring, preserving the anhydrous conditions and in ice bath of −18 °C. The reaction mixture is treated with N-bromosuccinimide (NBS, 1.4 equiv.): this operation should be done carefully, adding the NBS portion-wise in six equal fractions each 5-10 minutes. Meanwhile, in another anhydrous round-bottom flask, the amines 1-Boc-piperazine (1.2 equiv.) and triethylamine (TEA, 2 equiv.) are solubilized in dry. This solution is later added to the reaction flask, previously cooled again to −18 °C. After the addition of these last reagents, the reaction flask is brought out from the ice bath one more time and let react overnight at room temperature under magnetic stirring. The raw product is worked up through precipitation on hexane and $Et_2O$. This way a crude yellow oil to be purified by chromatography on silica gel is obtained.

v), lead to the obtaining of intermediate of formula (vi).

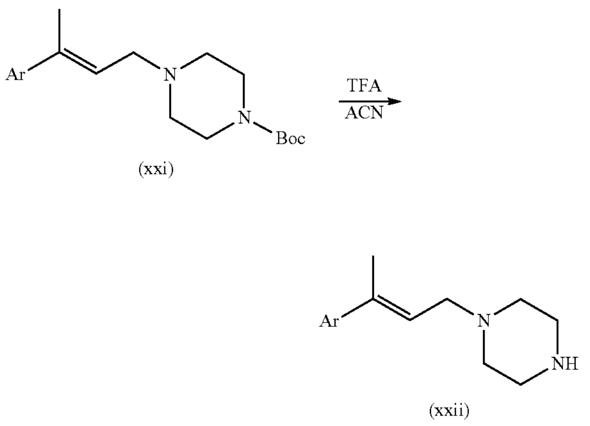

(xxi) (xxii)

Step (d). Into a vessel of the appropriate volume, the Boc-protected intermediate was dissolved in acetonitrile (ACN), and subsequently added trifluoroacetic acid (TFA, 5 equiv.) The reaction mixture was evaporated and the resulting de-Boc products were used without further purification.

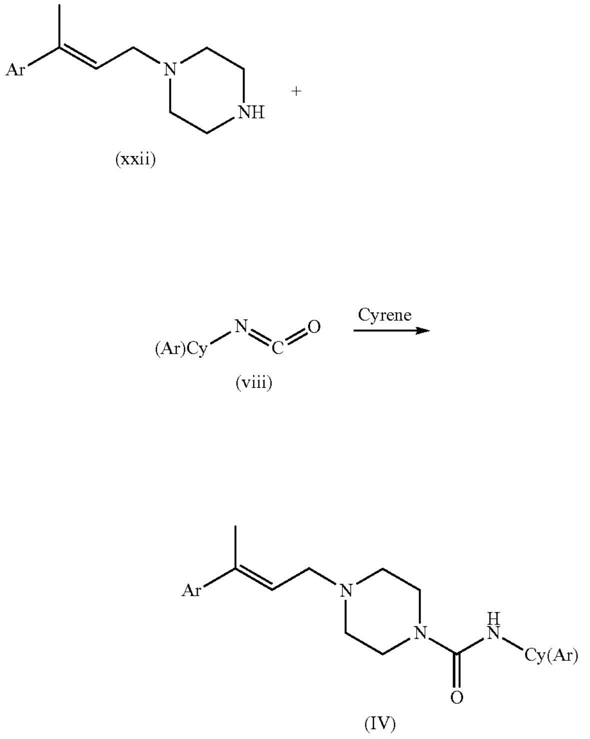

(xxii) (viii) (IV)

Step (e). In a one-neck round-bottom flask, a mixture of piperazine intermediate (1 equiv.) and the corresponding isocyanates (1.5 eqiv.) is solubilized in Cyrane under magnetic stirring. After 30 min, the crude product was purified by precipitation on extraction with ethyl acetate (AcOEt) to obtain the desired compound of formula (IV) was formed Compounds 26, 27, 28, 29 and 30 were prepared using the synthetic route described before, showing the substituent reported in Table 2:

TABLE 2

| No. | Ar | Cy(Ar) |
|---|---|---|
| 26 | 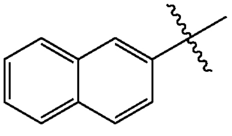 [SMILES: *c1ccc2ccccc2c1] | 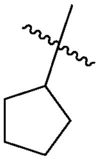 [SMILES: *C1CCCC1] |
| 27 | 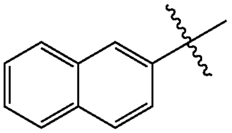 [SMILES: *c1ccc2ccccc2c1] | 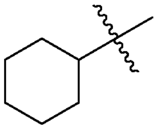 [SMILES: *C1CCCCC1] |
| 28 | 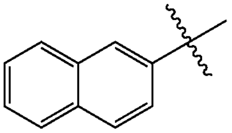 [SMILES: *c1ccc2ccccc2c1] | 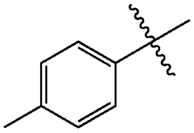 [SMILES: *c1ccc(C)cc1] |
| 29 | 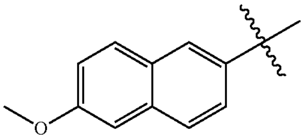 [SMILES: *c1ccc2cc(OC)ccc2c1] | 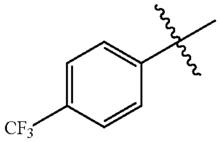 [SMILES: *c1ccc(C(F)(F)F)cc1] |
| 30 | 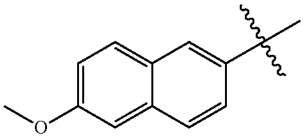 [SMILES: *c1ccc2cc(OC)ccc2c1] | 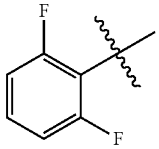 [SMILES: *c1c(F)cccc1F] |

Examples of Characterization of Compounds of Formula (III):

Characterization of compound 26: white solid, 90%, $R_f$=0.26 (DCM/MeOH 9:1), UHPLC-ESI-MS: $R_t$=2.33, m/z=378.2 $[M+H]^+$. $^1H$ NMR (300 MHz, $CDCl_3$) δ 7.84-7.78 (m, 4H), 7.56 (dd, J=1.9 Hz, J=8.6 Hz, 1H), 7.48-7.44 (m, 2H), 6.02 (dt, J=1.1 Hz, J=7.2 Hz, 1H), 4.07 (dd, J=6.8 Hz, J=13.5 Hz, 1H), 3.55-3.48 (m, 5H), 2.82-2.79 (m, 5H), 2.18 (d, J=0.9 Hz, 3H), 2.03-1.93 (m, 2H), 1.67-1.56 (m, 4H), 1.39-1.28 (m, 2H) ppm;

$^{13}C$ NMR (100 MHz, $CDCl_3$) δ 157.2, 141.0, 139.6, 133.2, 132.8, 128.1, 127.9, 127.5, 126.2, 126.0, 124.6, 124.0, 120.4, 55.6, 52.6, 51.7, 42.6, 33.4, 23.6, 16.4 ppm.

Characterization of compound 27: yellow oil, 36%, $R_f$=0.31 (DCM/MeOH 9:1), UHPLC-ESI-MS: $R_t$=2.48, m/z=392.2 $[M+H]^+$. $^1H$ NMR (300 MHz, $CDCl_3$) δ 7.82-7.73 (m, 4H), 7.56 (dd, J=1.8 Hz, J=8.6 Hz, 1H), 7.45-7.43 (m, 2H), 6.10 (t, J=7.0 Hz, 1H), 5.04 (s br, 1H), 3.70 (s, 5H), 3.60-3.53 (m, 1H), 2.96 (s, 5H), 2.10 (s, 3H), 1.90-1.86 (m, 2H), 1.69-1.65 (m, 2H), 1.59-1.55 (m, 1H), 1.32-1.25 (m, 2H), 1.15-1.07 (m, 3H) ppm;

$^{13}C$ NMR (100 MHz, $CDCl_3$) δ 156.8, 139.1, 136.0, 133.2, 132.9, 130.9, 128.2, 127.9, 127.5, 126.3, 126.1, 124.9, 124.1, 51.4, 50.8, 49.8, 41.8, 33.6, 25.5, 25.2, 16.4 ppm.

Characterization of compound 28: yellow oil, 12%, $R_f$=0.36 (DCM/MeOH 19:1), UHPLC-ESI-MS: $R_t$=2.42, m/z=452.2 $[M+H]^+$. $^1H$ NMR (300 MHz, $CDCl_3$) δ 7.76-7.68 (m, 3H), 7.57 (dt, J=1.8 Hz, J=9.0 Hz, 1H), 7.13-7.09 (m, 3H), 6.95-6.89 (m, 2H), 6.01 (t, J=7.2 Hz, 1H), 3.93 (s, 3H), 3.73-3.68 (m, 6H), 2.80-2.75 (m, 4H), 2.20 (d, J=5.0 Hz, 3H) ppm; $^{13}C$ NMR (100 MHz, $CDCl_3$) δ 159.1, 157.8 (d, J=6.1 Hz), 154.5, 145.1, 137.4, 135.1, 134.0, 129.7, 128.8, 128.2, 127.0, 126.8, 124.5, 119.1 (d, J=4.3 Hz), 115.6, 111.4, 105.5, 55.3, 52.1, 51.8, 43.4, 16.3 ppm.

Analytical, preparative HPLC and Electron Spray Ionization condition (ESI) mass spectra were performed on an Agilent uHPLC (1290 Infinity) and an Agilent Prep-HPLC (1260 Infinity) both equipped with a Diode Array Detector and a Quadrupole MSD using mixture gradients of formic acid/water/acetonitrile as system solvent. High-resolution electrospray ionization mass spectra (ESI-FTMS) were recorded on a Thermo LTQ Orbitrap (high-resolution mass spectrometer from Thermo Electron) coupled to an 'Accela' HPLC system supplied with a 'Hypersil GOLD' column (Thermo Electron).

$^1H$ NMR spectra Macherey Nagel precoated TLC aluminium sheets were recorded at room temperature on a Bruker Avance spectrometer operating at 300 MHz. Chemical shifts are given in ppm (δ) from tetramethylsilane as an internal standard or residual solvent peak. Significant $^1H$ NMR data are tabulated in the following order: multiplicity (s, singlet; d, doublet; t, triplet; q, quartet; m, multiplet; dd, doublet of doublets; dt, doublet of triplets; td, triplet of doublets; br, broad), coupling constant(s) in hertz, number of protons. Proton decoupled $^{13}C$ NMR data were acquired at 100 MHz. $^{13}C$ chemical shifts are reported in parts per million (δ, ppm). All NMR data were collected at room temperature (25 °C).

The nuclear magnetic resonance spectra ($^1H$ NMR and $^{13}C$ NMR) obtained for compounds 26, 27 and 30 are reported in FIGS. 1-6. In the spectra, the chemical shift (in ppm) is reported on the x-axis and the normalized intensity is reported on the y-axis.

Synthesis of the Compounds of Formula (I)—Compounds 4, 5, 10, 11

The compounds 4, 5, 10 and 11 are prepared through the synthetic route described below.

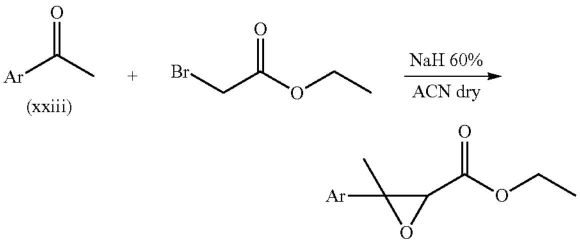

(xxiii)

(xxiv)

Step (a). In a one-neck round-bottom flask, preserving the anhydrous conditions, the Ar-chiton (1 equiv.) ethyl 2-bromoacetate (1.1 equiv.) and NaH (60%, 1.1 equiv.). were solubilized in dry ACN under magnetic stirring. The reaction is heated from room temperature to 60 °C.

After almost 1 hour the reaction has gone to completion. The reaction mixture is diluted and extracted three times with dichloromethane (DCM). The collected organic phases are washed with water, dried with sodium sulfate ($Na_2SO_4$) anhydrous, filtrated and evaporated to dryness at reduced pressure. The crude obtained was directly used for the subsequent reaction. Quantitative yield.

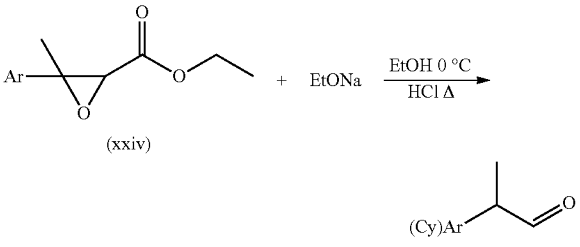

(xxiv)

(xxv)

Step (b). In a one-neck round-bottom flask, a mixture of Ar-epoxide (1 equiv.) is solubilized in EtOH under magnetic stirring and reacted with sodium ethoxide, preserving the anhydrous conditions and 0 °C temperature. After 10 min, $H_2O$ is added to promote the hydrolyzation. The mixture was acidified and heated until boiling. The reaction is diluted and extracted three times with diethyl ether ($Et_2O$). The collected organic phases are washed with water, dried with sodium sulfate ($Na_2SO_4$) anhydrous, filtrated and evaporated to dryness at reduced pressure. Without any other purification, the Ar-aldehyde is obtained in a yield of 50%.

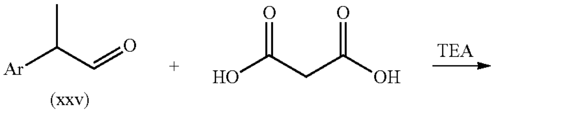

(xxv)

-continued

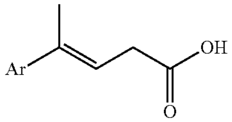

(xxvi)

Step (c). The Knoevenagel reaction was performed using a two-neck round-bottom flask. The mixture of Ar-aldehyde and malonic acid is solubilized in TEA as solvent. under magnetic stirring.

This reaction mixture is heated under reflux with an oil bath until a temperature of 90 °C. After almost six hours the reaction has gone to completion. The reaction mixture is diluted and extracted three times with diethyl ether ($Et_2O$) and alkaline water, the Aqueous phase is acidified and extracted with ethyl acetate (AcOEt). The collected organic phases are dried with sodium sulfate ($Na_2SO_4$) anhydrous, filtrated and evaporated to dryness at reduced pressure. The compound is obtained in a yield of 80-85% without any other purification.

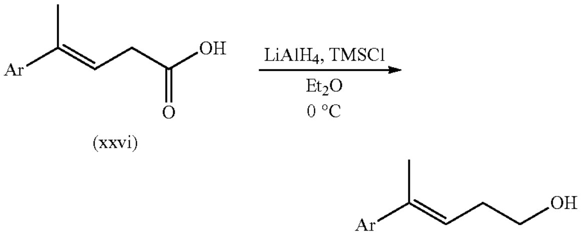

(xxvi)

(xxvii)

Step (d). In a one-neck round-bottom flask, preserving the anhydrous conditions, the Ar-acid (1 equiv.) from the previous synthetic step is solubilized in dry THF or $Et_2O$ under magnetic stirring. Once the solution is homogeneous, the reaction flask is put in a 0 °C ice bath. Afterwards, TMSC is added to active the carbonyl group and reduce the eq of lithium aluminum hydride. After 30 min lithium aluminum hydride ($LiAlH_4$, 0.7 equiv., 1M solution in dry THF) is added, slowly and dropwise, to the reaction mixture. After 1 hour, the reaction is quenched by adding a few drops of ethyl acetate (AcOEt) and, afterwards, some of ammonium chloride ($NH_4Cl$) saturated aqueous solution. The workup procedure follows three extractions with $Et_2O$ and washing of the collected organic phases with Brine. After that, the organic phase is dried with anhydrous $Na_2SO_4$, filtrated and evaporated to dryness at reduced pressure. Depending on the purity of the raw product, as reported below, this is either purified by chromatography on silica gel or used directly in the subsequent reaction.

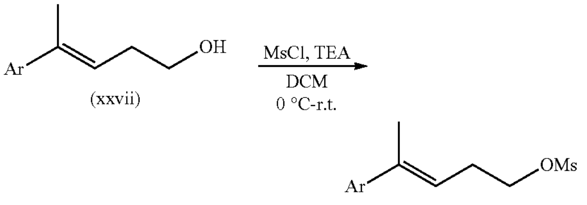

(xxvii)

(xxviii)

Step (e). Introduction of leaving group was performed in a one-neck round-bottom flask. A mixture of Ar-alcohol (1 equiv.), TEA (2 equiv.) and methanesulfonyl chloride (MsCl, 1.2 equiv.) is solubilized in DCM under magnetic stirring rom 0 °C to room temperature. After almost two hours the reaction has gone to completion. The reaction mixture is diluted and extracted three times with dichloromethane (DCM). The collected organic phases are washed with water, dried with sodium sulfate ($Na_2SO_4$) anhydrous, filtrated and evaporated to dryness at reduced pressure. The compound is obtained in quantitative yield without further purification.

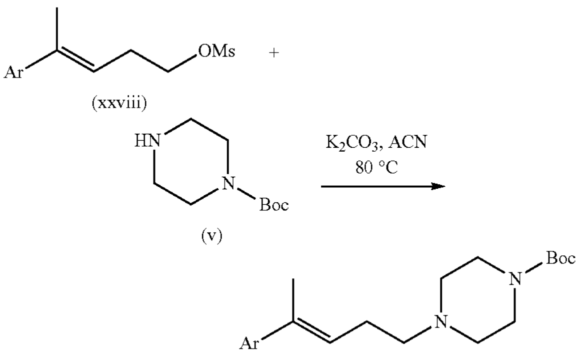

(xxviii) (v) (xxix)

Step (f). In a two-neck round-bottom flask, Boc-piperazine (1.5 equiv.), $K_2CO_3$ (3 equiv.) and Mesyl intermediate are added and solubilized in dry ACN. This reaction mixture is heated under reflux with an oil bath until a temperature of 80 °C. After almost ten hours the reaction has gone to completion. The reaction mixture is diluted and extracted three times with diethyl ether ($Et_2O$). The collected organic phases are washed with water, dried with sodium sulfate ($Na_2SO_4$) anhydrous, filtrated and evaporated to dryness at reduced pressure. The compound is obtained in quantitative yield without further purification.

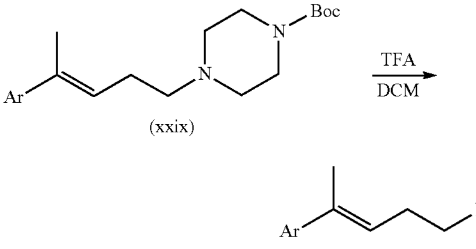

(xxix) (xxx)

Step (g). Into a vessel of the appropriate volume, the Boc-protected intermediate was dissolved in acetonitrile (ACN), and subsequently added trifluoroacetic acid (TFA, 5 equiv.). The reaction mixture was evaporated and the resulting de-Boc products were used without further purification.

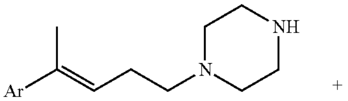

(xxx)

-continued

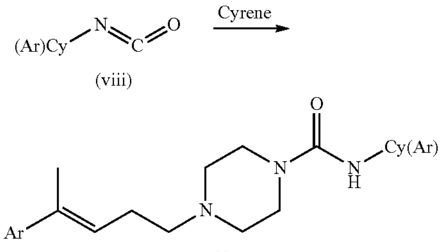

(viii) (V)

Step (h). In a one-neck round-bottom flask, a mixture of piperazine intermediate (1 equiv.) and the corresponding isocyanates (1.5 eqiv.) is solubilized in Cyrane under magnetic stirring. After 30 min, the crude product was purified by precipitation on extraction with ethyl acetate (AcOEt) to obtain the desired compound of formula (V) was formed

2. Anticancer Profile

Cell Viability after Compounds Treatment

Sulforhodamine B (SRB) assay was used to evaluate RPMI 8226 cell viability in vitro. It is a widely used method to evaluate cell viability and cytotoxicity. This method relies on the property of SRB, which binds stoichiometrically to proteins under mild acidic conditions. Thus, the amount of bound dye can be used as measure of cell proliferation.

Human RPMI 8226 and U87-MG cells were growth in culture medium (DMEM low glucose for U87-MG and RPMI 1640 for RPMI 8226), supplemented with 10% fetal bovine serum, 1% L-glutamine, 1% penicillin and streptomycin. Cells were maintained in a humidified incubator at 37 °C and 5% $CO_2$. For SRB assay, $1\times10^4$/well cells were seeded in a 96-well plate and were treated with increasing concentrations of the compounds (1-20 μM). After 24 hours, cells were fixed with 10% trichloroacetic acid and were stained with SRB solution. Excess of dye was removed by washing with 1% acetic acid. The protein-bound dye was then dissolved in 10 mM Tris base solution and absorbance was measured at 510 nm using a microplate reader.

Statistical analysis of the data obtained was performed using the one-way analysis of variance (ANOVA) and the Dunnet's post-hoc test. Values of $p<0.01$ (**) were considered statistically significant.

The results, expressed as the mean±standard deviation, represents the percentage of viable cells compared to untreated control (arbitrarily set to 100%).

Figure 7:
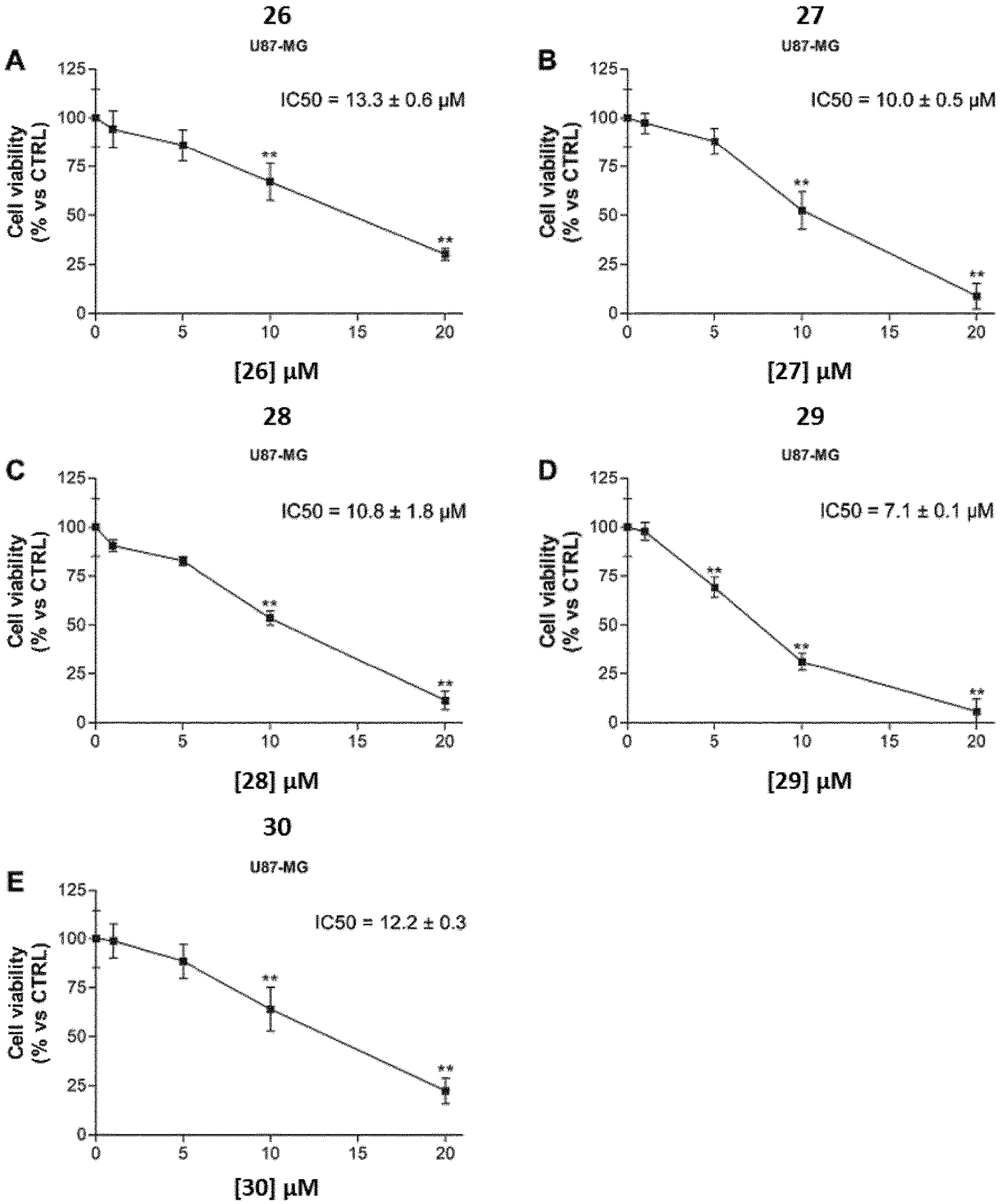
FIGS. 7 and 8 represent, respectively, the cell viability of U87-MG and RPMI 8226 cells.
Figure 8:
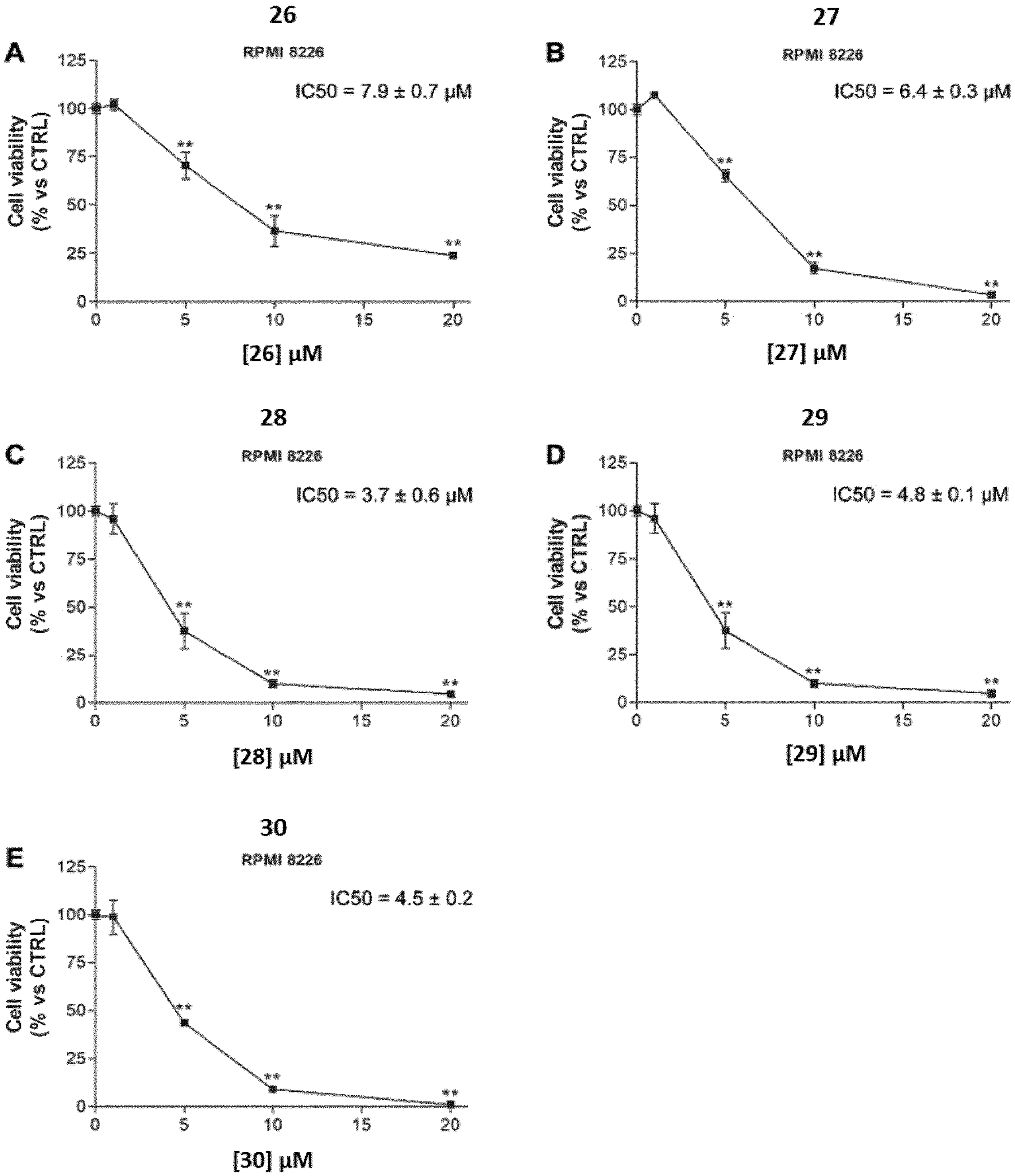

FIG. 7 represents the results obtained in U87-MG cells after treatment with compound 26 (A), 27 (B), 28 (C) 29 (D) and 30 (E). FIG. 8 represents the results obtained for RPMI 8226 cells after treatment with compound 26 (A), 27 (B), 28 (C) 29 (D) and 30 (E). Cells were treated for 24 hours with increasing concentrations of compounds (1, 5, 10 and 20 μM).

The results of FIG. 7 demonstrate that all compounds were able to reduce cell viability of U87-MG cells.

The $IC_{50}$ for U87-MG cells are 13.3±0.6 μM (compound 26), 10.0±0.5 μM (compound 27), 10.8±1.8 μM (compound 28), 7.1±0.1 μM (compound 29) and 12.2±0.3 μM (compound 30).

The results of FIG. 8 demonstrate that all compounds were able to reduce cell viability of RPMI 8226 cells.

The $IC_{50}$ for RPMI 8226 cells are 7.9±0.7 μM (compound 26), 6.4±0.3 μM (compound 27), 3.7±0.6 μM (compound 28), 4.8±0.1 μM (compound 29) and 4.5±0.2 μM (compound 30).

Table 3 reports IC20, IC50 and IC80 of U87-MG and RPMI 8226 cells. These results demonstrate that all analyzed compounds significantly impaired cell viability of both cell lines in a dose dependent manner compared to untreated controls.

TABLE 3

$IC_{20}$, $IC_{50}$ and $IC_{80}$ of U87-MG and RPMI 8226 cells in SRB assay

| Cell line | Compound | $IC_{20}$ (μM) | $IC_{50}$ (μM) | $IC_{80}$ (μM) |
|---|---|---|---|---|
| U87-MG | 26 | 26.3 ± 1.3 | 13.3 ± 0.6 | 6.7 ± 0.7 |
| | 27 | 15.7 ± 1.0 | 10.0 ± 0.5 | 6.4 ± 0.4 |
| | 28 | 21.7 ± 7.5 | 10.8 ± 1.8 | 5.4 ± 0.8 |
| | 29 | 12.7 ± 0.4 | 7.1 ± 0.1 | 3.9 ± 0.2 |
| | 30 | 21.4 ± 0.7 | 12.2 ± 0.3 | 6.9 ± 0.3 |
| RPMI 8226 | 26 | 22.6 ± 2.0 | 7.9 ± 0.7 | 3.9 ± 1.2 |
| | 27 | 9.5 ± 3.7 | 6.4 ± 0.3 | 4.2 ± 2.1 |
| | 28 | 7.1 ± 0.6 | 3.7 ± 0.6 | 1.9 ± 0.5 |
| | 29 | 8.1 ± 0.3 | 4.8 ± 0.1 | 2.9 ± 0.1 |
| | 30 | 7.3 ± 0.1 | 4.5 ± 0.2 | 2.9 ± 0.1 |

Cell Migration

The scratch wound healing assay evaluates the ability of cells to close a manually created gap on the cell monolayer in vitro. This assay is indicative of cell motility and the ability of cells to propagate locally.

Cells were seeded in 6-well plates and were incubated until reaching confluence. At this point, using a plastic tip, a scratch was manually created on the surface of the cell monolayer. Culture medium was then replaced with fresh medium with or without treatments. Cells were treated with increasing concentrations of the compounds (1-10 μM). Micrographs were taken immediately after the scratch (t0) and 24 hours later (t24). The area of the scratch was measured using ImageJ software and cell migration area was calculated by subtracting the t24 area from the t0 area.

Statistical analysis of the data obtained was performed using the one-way analysis of variance (ANOVA) and the Dunnet's post-hoc test. Values of $p<0.01$ (**) were considered statistically significant.

The results, expressed as the mean±standard deviation, represents the percentage of the cell migration area compared to untreated control (arbitrarily set to 100%).

Figure 9:
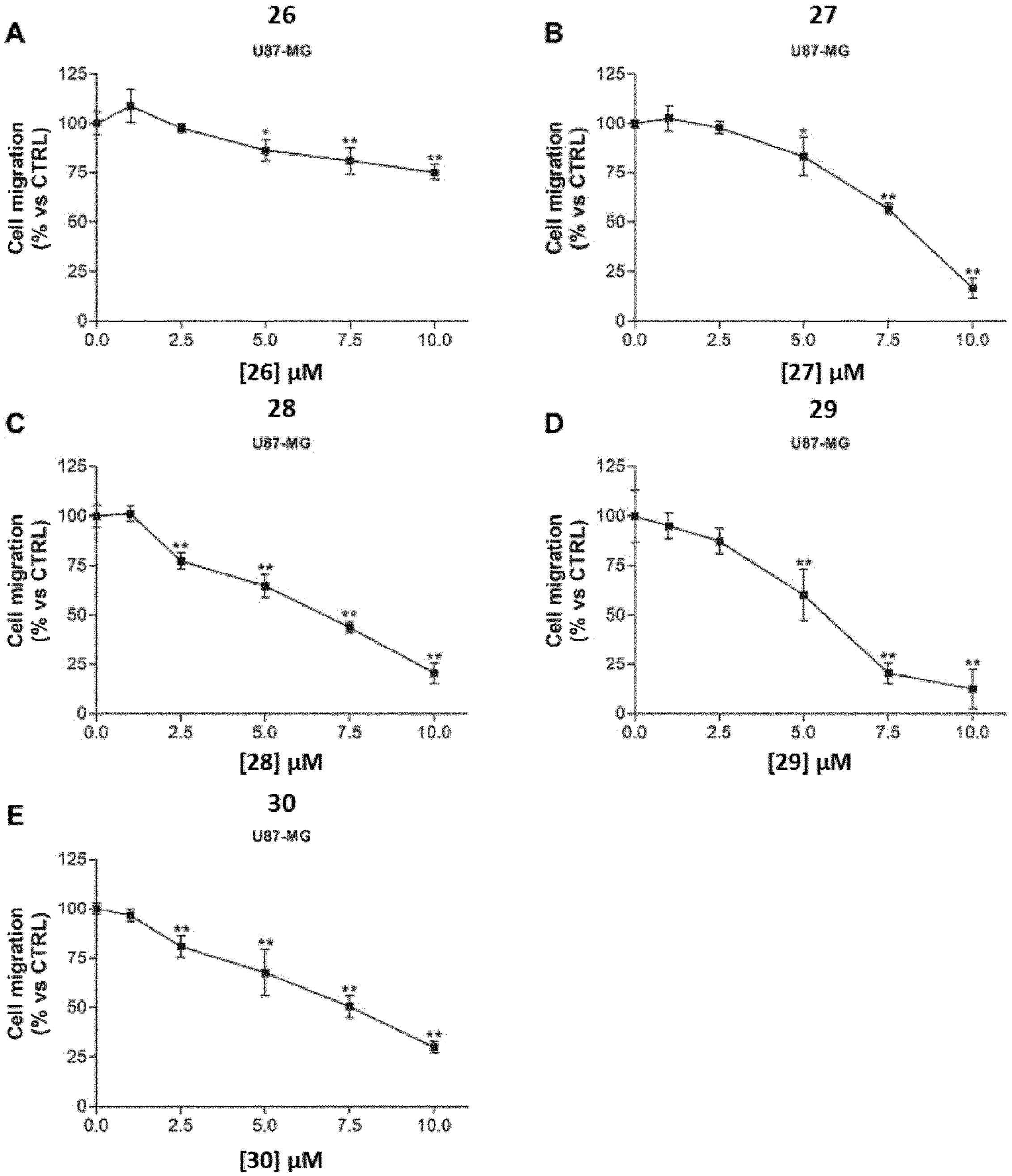
FIG. 9 represent cell migration assays on U87-MG cells.

The results of FIG. 9 demonstrate that compound 26 had a weak ability to reduce migration. Contrariwise compounds 27, 28, 29 and 30 are strong cell migration inhibitors and their effect was dose dependent.

Cell Invasion

Cell invasion is evaluated by Boyden Chamber. In Boyden chamber, cells attracted by a chemoattractant pass through a porous membrane coated with gelatine. This in vitro assay is indicative of the ability of cells to cross an extracellular substrate and invade surrounding tissues. U87-MG and RPMI cells were resuspended in FBS-free medium, with or without treatments. $IC_{20}$ obtained in SRB assay was used as compound treatment concentration, in order to not affect the invasion results with a too high mortality. $5\times10^3$ cells/well were seeded in the upper compartment of the Boyden chamber. In the lower compartment a complete medium supplemented with 10% FBS was placed. FBS was used as chemoattractant. Between the two compartments, a gelatine coated polycarbonate membrane with 8 μm pores was placed. The Boyden chamber, thus set up, was placed at 37 °C in an incubator for 24 hours (RPMI 8226 cells) or for 16 hours (U87-MG cells). After incubation membrane was removed and cells on the lower surface of the membrane were fixed and stained with Diffquick staining kit. Micrographs were taken and cells were counted using ImageJ software.

Statistical analysis of the data obtained was performed using the ANOVA and the Dunnet's post-hoc test. Values of $p<0.01$ (**) were considered statistically significant.

The results, expressed as the mean±standard deviation, represents the percentage of cells that are able to pass through the membrane compared to untreated control (arbitrarily set to 100%).

Figure 10:
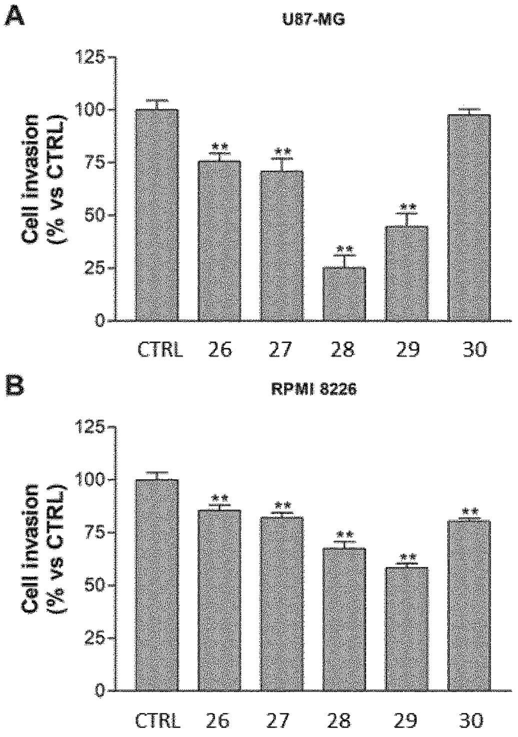
FIG. 10 represent cell invasion of U87-MG and RPMI 8226 cells.

The results of FIG. 10A demonstrate that compound 28 is very effective in reducing cell invasion of U87-MG. Compound 29 also reduced cell invasion, but it was less effective than compound 28. Compounds 26 and 27 had a weak effect against cell invasion of U87-MG, while compound 30 is not effective.

The results of FIG. 10B demonstrate that said compounds had ability to reduce cell invasion of RPMI 8226 cells. Compounds 26, 27 and 30 had a weak effect (approximatively 80% compared to untreated control). The reduction of cell invasion induced by compounds 28 and 29 was statistically significant, however lower than the one obtained in U87-MG cells.

These results demonstrate that compounds 28 and 29 are significantly able of inhibiting the invasion of U87-MG cells.

Proteasome Inhibitory Activity

Proteasome is a cellular complex responsible for the degradation of a high amount of regulatory, misfolded or damaged intracellular proteins. It is considered an important target for anticancer therapy.

Proteasome activity was evaluated by 7-Amido-4-Methylcoumarin fluorescent probe.

U87-MG and RPMI 8226 cells were cultured in 6 well-plates at $25\times10^4$ cells/well density and were treated with $IC_{50}$ concentration of each compound (calculated in SRB assay). After 24 hours of treatment, cells were collected and total protein extracts were obtained. Lysis buffer (5 mM Hepes pH 7.5, 150 mM NaCl, 10% glycerol, 1% Triton X100, 1.5 mM $MgCl_2$, 5 mM EGTA) was not supplemented with proteases and phosphatases inhibitors. Protein content was quantified using Bradford method. 40 μg of proteins were mixed with proteasome buffer (250 mM Hepes pH 7.5, 5 mM EDTA, 0.5% NP-40, 0.01% SDS) and 2.2 mM 7-Amido-4-Methylcoumarin. After 2 hours of incubation at 37 °C, fluorescence was quantified in a microplate reader (excitation 380 nm, emission 460 nm).

Statistical analysis of the data obtained was performed using the ANOVA and the Dunnet's post-hoc test. Values of $p<0.01$ (**) were considered statistically significant.

The results, expressed as the mean±standard deviation, represents the percentage of proteasome activity compared to untreated control (arbitrarily set to 100%).

Figure 11:
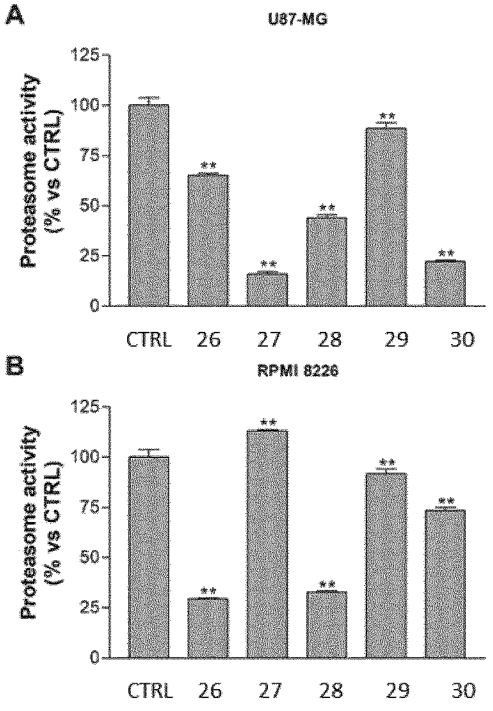
FIG. 11 represent the results of the proteasome activity in U87-MG and RPMI 8226 cells.

The results of FIG. 11A demonstrate that compounds 27 and 30 are strong proteasome inhibitors (inhibition greater than 50%) for U87-MG cells. Compounds 26 and 29 are less effective than the previous ones (approximatively 50% inhibition). Compound 29 has only a weak inhibitory effect.

The results of FIG. 11B demonstrate that compounds 26 and 28 are strong proteasome inhibitors (inhibition greater than 50%) for RPMI 8226 cells. Compounds 29 and 30 have only a weak inhibitory effect. Compound 27 has not an inhibitory effect.

These results demonstrate that compounds 26 and 28 are able of inhibiting the proteasome activity in two tumor cell lines that not only derive from different tumors but have also different biological characteristics. It is interesting point out that for compounds 27 and 30 t, the ability to inhibit the proteasome is cell line dependent. Finally, compound 29 has only weak inhibitory activity in both cell lines.

Neurotoxic Effect

Evaluation of NGF-induced neurite outgrowths was performed on dorsal root ganglia (DRG) of 15-day-old embryonic Sprague-Dawley rats. Briefly, DRG were aseptically collected and plated onto collagen coated dishes. DRG were cultured in $AN_2$ medium supplemented with 5 ng/mL NGF in a 5% $CO_2$ humidified incubator at 37 °C. DRG were treated after 2 hours with increasing concentrations of compounds, corresponding to $IC_{20}$, $IC_{50}$ and $IC_{80}$ in U87-MG SRB assay. Micrographs of DRG were taken after 24 and 72 hours of treatment and neurite elongation was manually measured using ImageJ software.

Statistical analysis of the data obtained was performed using the ANOVA and the Dunnet's post-hoc test. Values of $p<0.01$ (**) were considered statistically significant.

The results, expressed as the mean±standard deviation, represents the percentage of neurite outgrowth compared to untreated control (arbitrarily set to 100%).

According to this method of in vitro neurotoxicity evaluation, a compound can be considered neurotoxic if neurites length is less than 50% of the control.

Figure 12:
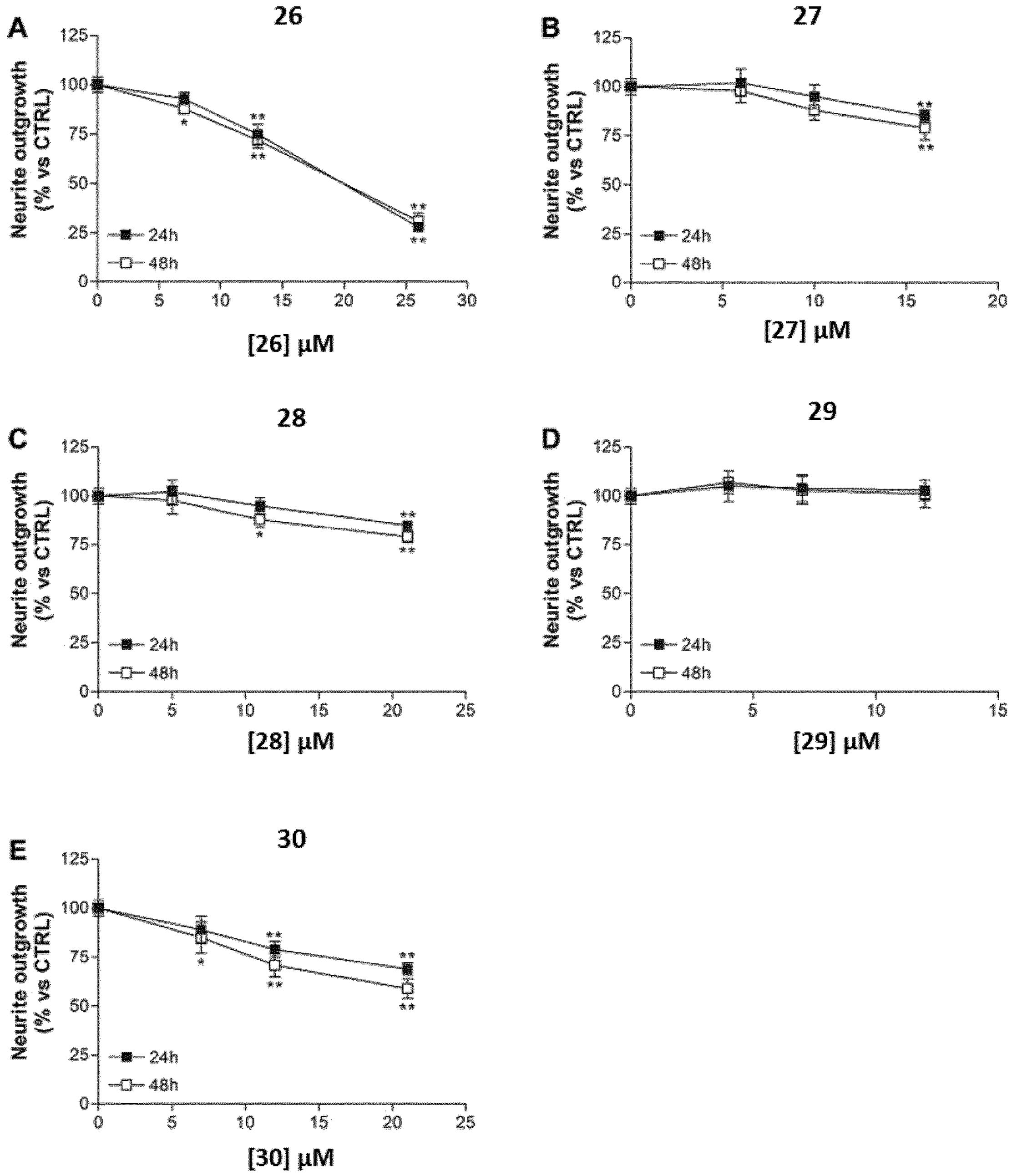
FIG. 12 Neurite outgrowth of embryonic rat DRG organotypic cultures.

FIG. 12 represents the results obtained with compound 26 (A), 27 (B), 28 (C) 29 (D) and 30 (E).

The results of FIG. 12 demonstrate that compound 26 is not neurotoxic up to 13 μM. Contrariwise, at the highest concentration evaluated it was found to be neurotoxic. Compounds 27, 28 and 29 are not neurotoxic at all evaluated concentrations and time points. Compound 30 significantly reduces the length of neurites, but the percentage is higher than 50% at all evaluated concentrations and can be considered not neurotoxic in vitro.

These results demonstrate that compounds 27, 28, 29 and 30 are not neurotoxic at all evaluated concentrations, while compound 26 is not neurotoxic only up to 13 μM.

The invention claimed is:

1. A compound of formula (I):

(I)

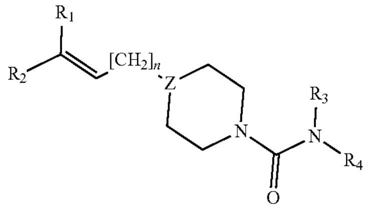

wherein:

Z is N or CH, n is 1, 2, 3, 4 or 5, $R_1$ is linear or branched C1-C3 alkyl, $R_2$ and $R_4$ are independently a substituted or unsubstituted aryl or a substituted or unsubstituted cyclic moiety, and $R_3$ is hydrogen or linear or branched C1-C3 alkyl.

2. The compound of formula (I) according to claim 1, wherein Z is N.

3. The compound of formula (I) according to claim 1, wherein n is 1 or 2.

4. The compound of formula (I) according to claim 1, wherein $R_3$ is hydrogen.

5. The compound of formula (I) according to claim 1, wherein $R_4$ is substituted or unsubstituted phenyl, naphthyl, biphenyl, binaphthyl or substituted or unsubstituted C5-C6 cycloalkyl.

6. The compound of formula (I) according to claim 5, wherein $R_4$ is unsubstituted cyclopentyl, unsubstituted cyclohexyl, phenyl, 4-methylphenyl, 2,6-difluorophenyl, or 4-trifluoromethylphenyl.

7. The compound of formula (I) according to claim 1, wherein $R_1$ is methyl.

8. The compound of formula (I) according to claim 1, wherein $R_2$ is substituted or unsubstituted phenyl or substituted or unsubstituted napthyl.

9. The compound of formula (I) according to claim 8, wherein $R_2$ is substituted or unsubstituted 2-napthyl having the following formula (II):

(II)

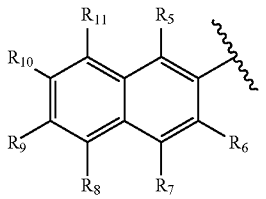

wherein, $R_5$, $R_6$, $R_7$, $R_8$, $R_9$, $R_{10}$ and $R_{11}$, are independently hydrogen, linear or branched C1-C4 alkyl, linear or branched C1-C4 alcoxy or halogen.

10. The compound of formula (I) according to claim 9, wherein $R_5$, $R_6$, $R_7$, $R_8$, $R_{10}$ and $R_{11}$, are hydrogen and $R_9$ is hydrogen, fluorine, chlorine or methoxy.

11. A compound selected from the following group:

(E)-4-(3-(6-fluoronaphthalen-2-yl)pent-2-en-1-yl)-N-(4-fluorophenyl)piperazine-1-carboxamide, (E)-N-(3,5-difluorophenyl)-4-(3-(6-methoxynaphthalen-2-yl)pent-2-en-1-yl)piperidine-1-carboxamide, (E)-N-cyclohexyl-4-(3-(6-fluoronaphthalen-2-yl)pent-2-en-1-yl)piperidine-1-carboxamide, (E)-4-(3-(naphthalen-2-yl)but-2-en-1-yl)-N-phenylpiperazine-1-carboxamide, (E)-4-(3-(naphthalen-2-yl)but-2-en-1-yl)-N-(4-(trifluoromethyl)phenyl)piperazine-1-carboxamide, (E)-N-cyclopentyl-4-(3-(naphthalen-2-yl)but-2-en-1-yl) piperazine-1-carboxamide, (E)-N-cyclohexyl-4-(3-(naphthalen-2-yl)but-2-en-1-yl) piperazine-1-carboxamide, (E)-4-(3-(naphthalen-2-yl)but-2-en-1-yl)-N-(p-tolyl)piperazine-1-carboxamide, (E)-4-(3-(6-methoxynaphthalen-2-yl)but-2-en-1-yl)-N-(4-(trifluoromethyl)phenyl)piperazine-1-carboxamide, (E)-N-(2,6-difluorophenyl)-4-(3-(6-methoxynaphthalen-2-yl)but-2-en-1-yl)piperazine-1-carboxamide, (E)-4-(4-(6-methoxynaphthalen-2-yl)pent-3-en-1-yl)-N-(4-(trifluoromethyl)phenyl)piperazine-1-carboxamide, and (E)-4-(4-(6-methoxynaphthalen-2-yl)pent-3-en-1-yl)-N-phenylpiperazine-1-carboxamide.

12. A process for the preparation of the compound of formula (I):

(I)

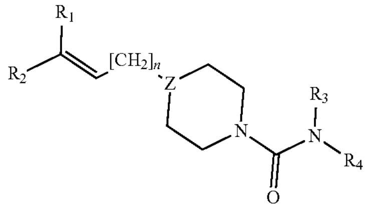

as claimed in claim 1, comprising the reaction of a compound of formula (A):

(A)

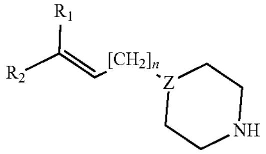

with a compound of formula (B):

(B)

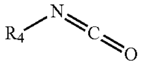

wherein n, Z, $R_1$, $R_2$, $R_3$ and $R_4$ have the same meaning of the compound of formula (I).

13. The process for the preparation of the compound of formula (I) according to claim 12, wherein compound (A) is prepared by a N-deprotection reaction of the compound of formula (A-1):

(A-1)

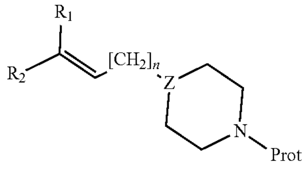

wherein Prot is a nitrogen protecting group.

14. The process for the preparation of the compound of formula (I) according to claim 13, wherein the compound (A-1) is prepared by a coupling reaction of the compound (A-2) or of the compound (A-3) with the compound (A-4):

(A-2)

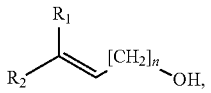

(A-3)

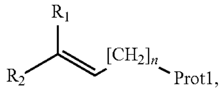

(A-4)

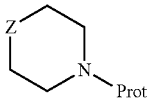

wherein Prot is a nitrogen protecting group and Prot1 is an hydroxyl protecting group.

15. The process for the preparation of the compound of formula (I) according to claim 14, wherein Prot1 is Mesyl group.

16. The process for the preparation of the compound of formula (I) according to claim 13, wherein Prot nitrogen protecting group is Boc.

17. A pharmaceutical composition comprising the compound of formula (I) according to claim 1 and at least one pharmaceutically acceptable excipient.

* * * * *